US012310956B2

(12) United States Patent
Osborne

(10) Patent No.: US 12,310,956 B2
(45) Date of Patent: *May 27, 2025

(54) TOPICAL ROFLUMILAST FORMULATION HAVING IMPROVED DELIVERY AND PLASMA HALF-LIFE

(71) Applicant: ARCUTIS BIOTHERAPEUTICS, Inc., Westlake Village, CA (US)

(72) Inventor: David W. Osborne, Fort Collins, CO (US)

(73) Assignee: ARCUTIS BIOTHERAPEUTICS, Inc., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/653,662

(22) Filed: May 2, 2024

(65) Prior Publication Data

US 2024/0285595 A1 Aug. 29, 2024

Related U.S. Application Data

(60) Continuation of application No. 18/353,869, filed on Jul. 17, 2023, now Pat. No. 12,005,052, which is a continuation of application No. 18/176,601, filed on Mar. 1, 2023, now Pat. No. 11,819,496, which is a continuation of application No. 17/402,051, filed on Aug. 13, 2021, now Pat. No. 12,005,051, which is a continuation of application No. 16/778,845, filed on Jan. 31, 2020, now Pat. No. 11,129,818, which is a continuation-in-part of application No. 16/136,804, filed on Sep. 20, 2018, now Pat. No. 10,940,142, which is a continuation of application No. 15/848,505, filed on Dec. 20, 2017, now Pat. No. 10,105,354, which is a continuation of application No. 15/676,356, filed on Aug. 14, 2017, now Pat. No. 9,884,050, which is a division of application No. 15/616,409, filed on Jun. 7, 2017, now Pat. No. 9,895,359.

(51) Int. Cl.
| | | |
|---|---|---|
| *A61K 31/44* | (2006.01) | |
| *A61K 9/00* | (2006.01) | |
| *A61K 45/06* | (2006.01) | |
| *A61K 47/06* | (2006.01) | |
| *A61K 47/10* | (2017.01) | |
| *A61K 47/14* | (2017.01) | |
| *A61K 47/24* | (2006.01) | |
| *A61P 17/06* | (2006.01) | |

(52) U.S. Cl.
CPC ............ *A61K 31/44* (2013.01); *A61K 9/0014* (2013.01); *A61K 45/06* (2013.01); *A61K 47/06* (2013.01); *A61K 47/10* (2013.01); *A61K 47/14* (2013.01); *A61K 47/24* (2013.01); *A61P 17/06* (2018.01)

(58) Field of Classification Search
CPC ......... A61K 31/44; A61K 47/10; C09K 15/06
See application file for complete search history.

(56) References Cited

U.S. PATENT DOCUMENTS

| | | |
|---|---|---|
| 4,482,537 A | 11/1984 | El-Menshawy et al. |
| 5,374,661 A | 12/1994 | Betlach, II |
| 5,712,298 A | 1/1998 | Amschler |
| 5,863,560 A | 1/1999 | Osborne |
| 6,056,955 A | 5/2000 | Fischetti et al. |
| 6,060,085 A | 5/2000 | Osborne |
| 6,106,848 A | 8/2000 | Preuilh et al. |
| 6,117,915 A | 9/2000 | Pereira et al. |
| 6,214,322 B1 | 4/2001 | Castro et al. |
| 7,470,791 B2 | 12/2008 | Kohl et al. |
| 7,951,398 B2 | 5/2011 | Dietrich et al. |
| 8,293,288 B2 | 10/2012 | Ma |
| 8,338,648 B2 | 12/2012 | Stock et al. |
| 8,377,663 B2 | 2/2013 | Lintner et al. |
| 8,536,206 B2 | 9/2013 | Kohl et al. |
| 8,618,142 B2 | 12/2013 | Kohl et al. |
| 8,884,034 B2 | 11/2014 | Daynard et al. |
| 9,205,044 B2 | 12/2015 | Linder |
| 9,649,302 B2 | 5/2017 | Vakkalanka |
| 9,884,050 B1 | 2/2018 | Osborne |
| 9,895,359 B1 | 2/2018 | Osborne |
| 9,907,788 B1 | 3/2018 | Osborne |
| 10,092,588 B2 | 10/2018 | Tamarkin |

(Continued)

FOREIGN PATENT DOCUMENTS

| | | |
|---|---|---|
| CN | 1655782 | 8/2005 |
| CN | 101061993 A | 10/2007 |

(Continued)

OTHER PUBLICATIONS

Sullivan DW Jr, Gad SC, Julien M. A review of the nonclinical safety of Transcutol(R), a highly purified form of diethylene glycol monoethyl ether (DEGEE) used as a pharmaceutical excipient. Food Chem Toxicol. 2014;72:40-50.
Helton DR, Osborne DW, Pierson SK, Buonarati MH, Bethem RA. Pharmacokinetic profiles in rats after intravenous, oral, or dermal administration of dapsone. Drug Metab Dispos. 2000;28(8):925-9.
Gad SC, Cassidy CD, Aubert N, Spainhour B, Robbe H. Nonclinical vehicle use in studies by multiple routes in multiple species. Int J Toxicol. 2006;25(6):499-521.
Chadha G, Sathigari S, Parsons DL, Jayachandra Babu R. In vitro percutaneous absorption of genistein from topical gels through human skin. Drug Dev Ind Pharm. 2011;37(5):498-505.
Ganem-Quintanar A, Lafforgue C, Falson-Rieg F, Buri P. Evaluation of the transepidermal permeation of diethylene glycol monoethyl ether and skin water loss. Int J Pharm. 1997; 147(2):165-71.

(Continued)

*Primary Examiner* — Theodore R. Howell
(74) *Attorney, Agent, or Firm* — ROTHWELL, FIGG, ERNST & MANBECK, P.C.

(57) ABSTRACT

The present invention is directed to methods for improving the therapeutic outcome of treatment with roflumilast. The therapeutic outcome is improved by consistent delivery and/or a longer plasma half-life of a topically administered roflumilast composition. The roflumilast composition preferably includes dicetyl phosphate, ceteth-10 phosphate, diethylene glycol I monoethyl ether, and/or hexylene glycol.

22 Claims, 12 Drawing Sheets

(56) References Cited

U.S. PATENT DOCUMENTS

| | | | |
|---|---|---|---|
| 10,105,354 B1 | 10/2018 | Osborne | |
| 10,172,841 B2 | 1/2019 | Osborne | |
| 10,940,142 B2 | 3/2021 | Osborne | |
| 10,987,290 B2 | 4/2021 | Wei | |
| 11,129,818 B2 | 9/2021 | Osborne et al. | |
| 11,534,493 B2 | 12/2022 | Osborne | |
| 11,707,454 B2 | 7/2023 | Berk | |
| 11,793,796 B2 | 10/2023 | Osborne | |
| 11,819,496 B2 | 11/2023 | Osborne | |
| 11,992,480 B2 * | 5/2024 | Osborne | A61P 11/08 |
| 12,005,051 B2 * | 6/2024 | Osborne | A61K 9/08 |
| 12,005,052 B2 * | 6/2024 | Osborne | A61K 9/0014 |
| 12,011,437 B1 * | 6/2024 | Osborne | C09K 15/06 |
| 12,016,848 B2 * | 6/2024 | Osborne | A61K 9/0014 |
| 12,042,487 B2 * | 7/2024 | Osborne | A61K 9/122 |
| 12,042,558 B2 * | 7/2024 | Osborne | A61K 31/44 |
| 2005/0112162 A1 | 5/2005 | Drader | |
| 2005/0244339 A1 | 11/2005 | Jauernig et al. | |
| 2006/0084684 A1 | 4/2006 | Bolle | |
| 2006/0110415 A1 | 5/2006 | Gupta | |
| 2006/0153905 A1 | 7/2006 | Carrara | |
| 2006/0204452 A1 | 9/2006 | Lathrop et al. | |
| 2006/0204526 A1 | 9/2006 | Lathrop | |
| 2006/0234006 A1 | 10/2006 | Terra | |
| 2007/0048241 A1 | 3/2007 | Obukowho et al. | |
| 2007/0098660 A1 | 5/2007 | Taneri et al. | |
| 2007/0207107 A1 | 9/2007 | Winckle et al. | |
| 2007/0258935 A1 | 11/2007 | McEntire et al. | |
| 2007/0259009 A1 | 11/2007 | Linder | |
| 2007/0287689 A1 | 12/2007 | Harada | |
| 2008/0020005 A1 | 1/2008 | Chang et al. | |
| 2008/0039405 A1 | 2/2008 | Langley | |
| 2008/0045572 A1 | 2/2008 | Linder | |
| 2008/0280958 A1 | 11/2008 | Bolle et al. | |
| 2009/0104132 A1 | 4/2009 | Segura-Orsoni | |
| 2009/0214628 A1 | 8/2009 | De Rijk | |
| 2009/0215836 A1 | 8/2009 | Beume | |
| 2009/0220583 A1 | 9/2009 | Pereswetoff-Morath et al. | |
| 2011/0117182 A1 | 5/2011 | Ahluwalia et al. | |
| 2011/0212157 A1 | 9/2011 | Edelson et al. | |
| 2012/0252793 A1 | 10/2012 | Bream et al. | |
| 2013/0005816 A1 | 1/2013 | Chen | |
| 2013/0017282 A1 | 1/2013 | Ma | |
| 2013/0018104 A1 | 1/2013 | Lathrop et al. | |
| 2013/0217742 A1 | 8/2013 | Yang | |
| 2014/0112991 A1 | 4/2014 | Johnson et al. | |
| 2014/0275184 A1 | 9/2014 | Jones et al. | |
| 2014/0275265 A1 | 9/2014 | Mattison | |
| 2014/0296191 A1 | 10/2014 | Patel et al. | |
| 2014/0303215 A1 | 10/2014 | Bolle et al. | |
| 2015/0099752 A9 | 4/2015 | Bernal Anchuela et al. | |
| 2015/0297601 A1 | 10/2015 | Henkin | |
| 2016/0030435 A1 | 2/2016 | Henkin | |
| 2017/0152273 A1 | 6/2017 | Merchant | |
| 2017/0266289 A1 | 9/2017 | Lipari | |
| 2018/0353490 A1 | 12/2018 | Osborne | |
| 2019/0091333 A1 | 3/2019 | Osborne | |
| 2019/0175491 A1 | 6/2019 | Abraham et al. | |
| 2019/0365642 A1 | 12/2019 | Osborne et al. | |
| 2020/0155524 A1 | 5/2020 | Welgus et al. | |
| 2020/0163944 A1 | 5/2020 | Osborne et al. | |
| 2021/0161870 A1 | 6/2021 | Welgus et al. | |
| 2021/0275509 A1 | 9/2021 | Welgus et al. | |
| 2021/0386719 A1 | 12/2021 | Osborne et al. | |
| 2022/0211730 A1 | 7/2022 | Osborne et al. | |
| 2023/0091358 A1 | 3/2023 | Osborne et al. | |
| 2023/0201177 A1 | 6/2023 | Osborne | |
| 2023/0285319 A1 | 9/2023 | Osborne et al. | |
| 2023/0310345 A1 | 10/2023 | Osborne et al. | |

FOREIGN PATENT DOCUMENTS

| | | |
|---|---|---|
| CN | 101854907 | 10/2010 |
| CN | 112384199 | 2/2021 |
| EP | 1511516 | 3/2005 |
| JP | 2005529930 A | 10/2005 |
| JP | 2007119432 A | 5/2007 |
| JP | 2007533606 A | 11/2007 |
| JP | 2011219364 A | 11/2011 |
| JP | 2012532871 A | 12/2012 |
| WO | 9501338 | 1/1995 |
| WO | 9810768 | 3/1998 |
| WO | 2003099334 | 12/2003 |
| WO | WO 2005/016296 A1 | 2/2005 |
| WO | 2005115322 | 12/2005 |
| WO | 2006073559 A1 | 7/2006 |
| WO | 2008009616 A2 | 1/2008 |
| WO | 2009034537 A2 | 3/2009 |
| WO | 2009069006 A2 | 6/2009 |
| WO | 2013030789 | 3/2013 |
| WO | 2013081565 | 6/2013 |
| WO | 2014055801 | 4/2014 |
| WO | 2014130922 | 8/2014 |
| WO | 2014201541 | 12/2014 |
| WO | 2015132708 | 9/2015 |
| WO | 2016033308 | 3/2016 |
| WO | 2017216738 | 12/2017 |
| WO | 2018144093 A2 | 8/2018 |
| WO | 2018226584 | 12/2018 |
| WO | 2019060379 | 3/2019 |
| WO | 2021045804 | 3/2021 |

OTHER PUBLICATIONS

Dugard PH, Walker M, Mawdsley SJ, Scott RC. Absorption of some glycol ethers through human skin in vitro. Environ Health Perspect. 1984;57:193-7.

Koprda V, Bohacik L, & Hadgraft J Permeation of a Pyridoindol structure substance from the Transcutol/water/azone cosolvent system. In 5th International conference: Perspectives in Percutaneous Penetration. vol. 5B, pp. 163-164; 1997.

Ritschel WA, Hussain AS. In vitro skin penetration of griseofulvin in rat and human skin from an ointment dosage form. Arzneimittelforschung. 1988;38(11):1630-2.

Bialik W, Walkers KA, Brain KR, Hadgraft J. Some factors affecting the in vitro penetration of ibuprofen through human skin. Int J Pharm. 1993;92:219-23.

Yazdanian M, Chen E. The effect of diethylene glycol monoethyl ether as a vehicle for topical delivery of ivermectin. Vet Res Commun. 1995; 19(4):309-19.

Bjorklund S, et al. The effects of polar excipients transcutol and dexpanthenol on molecular mobility, permeability, and electrical impedance of the skin barrier. J Colloid Interface Sci. 2016;479:207-20.

Benson HA. Transdermal drug delivery: penetration enhancement techniques. Curr Drug Deliv. 2005;2(1):23-33.

Gwak HS, Kim SU, Chun IK. Effect of vehicles and enhancers on thein vitro permeation of melatonin through hairless mouse skin. Arch Pharm Res. 2002;25(3):392-6.

Harrison JE, Watkinson AC, Green DM, Hadgraft J, Brain K. The relative effect of azone and Transcutol on permeant diffusivity and solubility in human stratum corneum. Pharm Res. 1996; 13(4):542-6.

Otto A, Wiechers JW, Kelly CL, Hadgraft J, du Plessis J. Effect of penetration modifiers on the dermal and transdermal delivery of drugs and cosmetic active ingredients. Skin Pharmacol Physiol. 2008;21(6):326-34.

Bonina FP, Montenegro L. Effects of some non-toxic penetration enhancers on in vitro heparin skin permeation from gel vehicles. Int J Pharm. 1994;111(2):191-6.

Puglia C, Bonina F, Trapani G, Franco M, Ricci M. Evaluation of in vitro percutaneous absorption of lorazepam and clonazepam from hydro-alcoholic gel formulations. Int J Pharm.2001;228(1-2):79-87.

Godwin DA, Kim NH, Felton LA. Influence of Transcutol CG on the skin accumulation and transdermal permeation of ultraviolet absorbers. Eur J Pharm Biopharm. 2002;53(1):23-7.

Ritschel WA, Panchagnula R, Stemmer K, Ashraf M. Development of an intracutaneous depot for drugs. Binding, drug accumulation and retention studies, and mechanism of depot. Skin Pharmacol. 1991;4(4):235-45.

(56) References Cited

OTHER PUBLICATIONS

Remane Y, Leopold CS, Maibach HI. Percutaneous penetration of methyl nicotinate from ointments using the laser Doppler technique: bioequivalence and enhancer effects. J Pharmacokinet Pharmacodyn. 2006;33(6):719-35.
Panchagnula R, Ritschel WA. Development and evaluation of an intracutaneous depot formulation of corticosteroids using Transcutol as a cosolvent: in-vitro, ex-vivo and in-vivo rat studies. J Pharm Pharmacol. 1991;43(9):609-14.
Cho YA, Gwak HS. Transdermal delivery of ketorolac tromethamine: effects of vehicles and penetration enhancers. Drug Dev Ind Pharm. 2004;30(6):557-64.
Salimi A, Hedayatipour N, Moghimipour E. The effect of various vehicles on the naproxen permeability through rat skin: a mechanistic study by DSC and FT-IR techniques. Adv Pharm Bull. 2016;6(1):9-16.
Moghadam SH, Saliaj E, Wettig SD, Dong C, Ivanova MV, Huzil JT, et al. Effect of chemical permeation enhancers on stratum corneum barrier lipid organizational structure and interferon alpha permeability. Mol Pharm. 2013;10(6):2248-60.
Watkinson AC, Hadgraft J, Bye A. Aspects of the transdermal delivery of prostaglandins. Int J Pharm. 1991;74(2-3):229-36.
Gwak H, Chun I. Effect of vehicles and penetration enhancers on the in vitro percutaneous absorption of tenoxicam through hairless mouse skin. Int J Pharm. 2002;236(1-2):57-64.
Gwak HS, Oh IS, Chun IK. Transdermal delivery of ondansetron hydrochloride: effects of vehicles and penetration enhancers. Drug Dev Ind Pharm. 2004;30(2): 187-94.
Chang RK, Raw A, Lionberger R, Yu L. Generic development of topical dermatologic products: formulation development, process development, and testing of topical dermatologic products. AAPS J. 2013; 15(1):41-52.
Choi JS, Cho YA, Chun IK, Jung SY, Gwak HS. Formulation and evaluation of ketorolac transdermal systems. Drug Deliv. 2007; 14(2):69-74.
Hirata K, Helal F, Hadgraft J, Lane ME. Formulation of carbenoxolone for delivery to the skin. Int J Pharm. 2013;448(2):360-5.
Hirata K, Mohammed D, Hadgraft J, Lane ME. Influence of lidocaine hydrochloride and penetration enhancers on the barrier function of human skin. Int J Pharm. 2014;477(1-2):416-20.
Mura P, Faucci MT, Bramanti G, Corti P. Evaluation of transcutol as a clonazepam transdermal permeation enhancer from hydrophilic gel formulations. Eur J Pharm Sci. 2000;9(4):365-72.
Kim KH, Gwak HS. Effects of vehicles on the percutaneous absorption of donepezil hydrochloride across the excised hairless mouse skin. Drug Dev Ind Pharm. 2011;37(9):1125-30.
Rhee YS, Huh JY, Park CW, Nam TY, Yoon KR, Chi SC, et al. Effects of vehicles and enhancers on transdermal delivery of clebopride. Arch Pharm Res. 2007;30(9):1155-61.
Touitou E, Levi-Schaffer F, Shaco-Ezra N, Ben-Yossef R, Fabin B. Enhanced permeation of theophylline through the skin and its effect on fibroblast proliferation. Int J Pharm. 1991;70(1-2):159-66.
Touitou E, Levi-Schaffer F, Dayan N, Alhaique F, Riccieri F. Modulation of caffeine skin delivery by carrier design: liposomes versus permeation enhancers. Int J Pharm. 1994; 103(2):131-6.
Fabin B, Touitou E. Localization of lipophilic molecules penetrating rat skin in vivo by quantitative autoradiography. Int J Pharm. 1991;74(1):59-65.
Ayala-Bravo HA, Quintanar-Guerrero D, Naik A, Kalia YN, Cornejo-Bravo JM, Ganem-Quintanar A. Effects of sucrose oleate and sucrose laureate on in vivo human stratum corneum permeability. Pharm Res. 2003;20(8):1267-73.
Csizmazia E, Erős G, Berkesi O, Berkó S, Szabó-Révész P, Csányi E. Penetration Enhancer effect of sucrose laurate and Transcutol on ibuprofen. J Drug Deliv Sci Technol. 2011;21(5):411-415.
Cazares-Delgadillo J, Naik A, Kalia YN, Quintanar-Guerrero D, Ganem-Quintanar A. Skin permeation enhancement by sucrose esters: a pH-dependent phenomenon. Int J Pharm. 2005;297(1-2):204-212.

Gungor S, Bergisadi N. Effect of penetration enhancers on in vitro percutaneous penetration of nimesulide through rat skin. Pharmazie. 2004;59(1):39-41.
Barakat NS. Evaluation of glycofurol-based gel as a new vehicle for topical application of naproxen. AAPS PharmSciTech. 2010; 11(3):1138-46.
Javadzadeh Y, Hamishehkar H. Enhancing percutaneous delivery of methotrexate using different types of surfactants. Colloids Surf B Biointerfaces. 2011;82(2):422-6.
Senyigit T, Padula C, Ozer O, Santi P. Different approaches for improving skin accumulation of topical corticosteroids. Int J Pharm. 2009;380(1-2):155-60.
Berkó S, et al.Monitoring of skin penetration and absorption with a new in vivo experimental model. Farmacia. 2014;62(6): 1157-63.
Tiossi RF, et al. In vitro and in vivo evaluation of the delivery of topical formulations containing glycoalkaloids of Solanum lycocarpum fruits. Eur J Pharm Biopharm. 2014;88(1):28-33.
Ritschel WA, Barkhaus JK. Use of sorption promoters to increase systemic absorption of coumarin from transdermal drug delivery systems. Arzneimittelforschung. 1988;38(12): 1774-7.
Ritschel WA, Barkhaus JK. Feasibility study for transdermal delivery of meperidine. Methods Find Exp Clin Pharmacol. 1988; 10(7):461-466.
Shaaya AN, Kraus C, Bauman DH, Ritschel WA. Pharmacokinetics and bioavailability of papaverine HCl after intravenous, intracorporeal and penis topical administration in beagle dogs. Methods Find Exp Clin Pharmacol. 1992; 14(5):373-8.
Rougier A, Dupuis D, Lotte C, Roguet R, & H. Schaefer (1983) In vivo correlation between stratum corneum reservoir function and percutaneous absorption. J Invest Dermatol 81(275-278):275, 278; 1983.
Sutton et al., "Characterization of a Liquid Crystal Stabilized Pharmaceutical Oil-in-Water Emulsion Optimized for Skin Delivery", Journal of Cosmetics, Dermatological Sciences and Applications, vol. 8, No. 4, Nov. 2018, pp. 207-217.
V. Koprda et al., Skin Penetration Studies of Transcutol Using Radiotracer Technique, GRC (1995), 10 pgs.
Osborne et al., "Skin Penetration and Permeation Properties of Transcutol®—Neat or Diluted Mixtures", AAPS PharmaSCITECH, vol. 19, No. 8, Nov. 2018, pp. 3512-3533.
Office Action issued in U.S. Appl. No. 18/453,674 dated Oct. 27, 2023 (13 pages).
Office Action issued in U.S. Appl. No. 17/155,679 dated Feb. 5, 2024 (9 pages).
Office Action issued in U.S. Appl. No. 18/345,692 dated Oct. 26, 2023 (68 pages).
Office Action issued in U.S. Appl. No. 18/345,732 dated Jan. 24, 2024 (12 pages).
Office Action issued in U.S. Appl. No. 18/345,760 dated Oct. 26, 2023 (19 pages).
Office Action issued in U.S. Appl. No. 18/353,870 dated Jan. 12, 2024 (10 pages).
Office Action issued in U.S. Appl. No. 18/353,869 dated Sep. 18, 2023 (7 pages).
Notification of Certification of Invalidity, Unenforceability, and/or Noninfringement for U.S. Pat. Nos. 9,884,050; 9,907,788; 10,940,142; 11,129,818; 11,793,796; and 11,819,496 Pursuant to § 505(j)(2)(B)(iv) of the Federal Food, Drug, & Cosmetic Act, Feb. 13, 2024.
Akhtar et al., "Exploring preclinical and clinical effectiveness of nanoformulations in the treatment of atopic dermatitis: Safety aspects and patent reviews," Bulletin of Faculty of Pharmacy, Cairo University 55 (2017), 1-10.
Bardin P et al. "Roflumilast for asthma: Efficacy findings in mechanism of action studies." Pulmonary Pharmacology & Therapeutics, vol. 35, Aug. 19, 2015, S4-S10.
Brown, "Treating COPD with PDE 4 inhibitors", International Journal of COPD 2007: 2(4) 517-533.
Examination Report cited in India Application No. 20194705011 dated Jul. 9, 2021. 6 pages.
Examination Report cited in India Application No. 202047016247 dated Jun. 28, 2021. 4 pages.
Final Office Action issued in U.S. Appl. No. 15/712,900 dated May 23, 2022. 14 pages.

(56) References Cited

OTHER PUBLICATIONS

Huang, J. et al., "Pharmacokinetics of single- and multiple-dose roflumilast: an open-label, three-way crossover study in healthy Chinese volunteers." Drug Design, Development and Therapy, 2018(12). pp. 4047-4057.
International Search Report and Written Opinion cited in PCT/US2018/051691 dated Nov. 22, 2018, 11 pages.
International Preliminary Report on Patentability and Written Opinion cited PCT/US2018/051691 dated Mar. 24, 2020. 6 pages.
International Preliminary Report on Patentability and Written Opinion cited in PCT/US2018/051691 dated Apr. 2, 2020. 8 pages.
International Search Report issued in PCT/US2021/031144 dated Sep. 21, 2021. 2 pages.
Ip.com translation KR1999-0015251 A, printed 2022 (year2022), 1 page.
Julian N. Mayba et al. Review of Atopic Dermatitis and Topical Therapies:, Journal of Cutaneous Medicine and Surgery, BC Decker Inc. Ca. vol. 21 No. 3 Dec. 27, 2016, pp. 227-236.
Karande et al., "Enhancement of transdermal drug delivery via synergistic action of chemicals", Biochimica Et Biophysica Acta, 1788 (2009), pp. 2632-2373.
Kawamatawong, "Roles of roflumilast, a selective phosphodiesterase 4 inhibitor in airway diseases," J. Thorac Dis 2017. 9(4). 1144-1154.
Kircik, L et al., "Rational Vehicle Design Ensures Targeted Cutaneous Steroid Delivery." Journal of Clinical and Aesthetic Dermatology 10(2). Feb. 2017. pp. 12-19.
Lorimer, "Thermodynamics of solubility in mixed solvent systems", Pure & Appl. Chem., 1993, vol. 65, 2, pp. 183-191.
Minghetti et al., "Ex Vivo Study of Transdermal Permeation of Four Diclofenac Salts from Different Vehicles", Journal of Pharmaceutical Sciences, vo. 96, No. 4, Apr. 2007, pp. 814-823.
Nair et al., "Basic considerations in the dermatokinetics of topical formulations", Brazilian Journal of Pharmaceutical Sciences, vol. 43, No. 3, Jul./Sep. 2013, pp. 423-434.
Notification of Transmittal of the International Search Report and the Written Opinion of the International Searching Authority cited in PCT/US2020/29008 dated Jul. 6, 2020. 12 pages.
Notification of Transmittal of the International Search Report and Written Opinion cited in PCT/US2019/034640 dated Dec. 4, 2019, 10 pages.
Notification of Transmittal of the International Search Report and the Written Opinion of the International Searching Authority cited in PCT/US2021/015740 dated Apr. 23, 2021. 17 pages.
Notification of Transmittal of the International Search Report and Written Opinion of the International Searching Authority issued in PCT/US2022/013344 dated Jun. 9, 2022, 16 pages.
Notification of Transmittal of the International Search Report and the Written Opinion of the International Searching Authority issued in PCT/US2021/061871, dated Apr. 5, 2022. 12 pages.
Notification of Transmittal of the International Search Report and Written Opinion cited in PCT/US2019/034640, dated Dec. 4, 2019, 14 pages.
Office Action issued in MX/a/2019/014741 dated Nov. 4, 2022 (7 pages).
Osborne, "Diethylene glycol monoethyl ether: an emerging solvent in topical dermatology products", J. Cosmet Dermatol, Dec. 2011, 10(4), pp. 324-329.
Pathan et al., "Chemical Penetration Enhancers for Transdermal Drug Delivery Systems", Tropical Journal of Pharmaceutical Research, Apr. 2009, 8(2), pp. 173-179.
Patzelt et al., "Hair follicles, their disorders and their opportunities", Drug Discovery Today: Disease Mechanisms, vol. 5, Issue 2, Summer 2008, pp. e173-e181.
PCT International Search Report and Written Opinion issued in PCT/US2018/0358584 on Aug. 17, 2018, 12 pages.
Pudipeddi et al., "Trends in Solubility of Polymorphs", Journal of Pharmaceutical Sciences, May 2005, vol. 94, Issue 5, pp. 929-939, Abstract only.
Shakeel et al. "Solubilization behavior of paracetamol in Transcutol—water mixtures at (298.15 to 333.15) K," Journal of Chemical & Engineering Data 58:3551-3556, 2013.
Sikarra et al., "Techniques for Solubility Enhancement of Poorly Soluble Drugs: An Overview", Journal of Medical Pharmaceutical and Allied Sciences, (2012), 01; pp. 1-22.
Snape et al., "A phase I randomized trial to assess the effect on skin infiltrate thickness and tolerability of topical phosphodiesterase inhibitors in the treatment of psoriasis vulgaris using a modified psoriasis plaque test", British Journal of Dermatology (2016) 175, pp. 479-486.
Special Chem "Ethoxydiglycol ," printed 2019; https://cosmetics.specialchem.com/inci/ethoxydiglycol.
Tradename (roflumilast) Tablets NDA 22-522, Summary of Basis for the Recommended Action from Chemistry, Manufacturing, and Controls, Forest Research Institute, Inc., Reference ID 2901509, Jul. 2009, 3 pages.
Translation Abstract. of Office Action for Chinese Patent Application No. 201810581282.7 dated Oct. 22, 2019; 13 pages.
Wikipedia "Corticosteroid," last edited Nov. 15, 2019; https://en.wikipedia.org/wiki/Corticosteroid.
Wittmann et al. "Phosphodiesterase 4 Inhibition in the Treatment of Psoriasis, Psoratic Arthritis and Other Chronic Inflammatory Diseases". Dermatol Ther(Heidelb) (2013) 3:1-15.
E P Bezuglaya et al., "Water-Hexylene Glycol System as a Potential Medicinal Base", Pharmaceutical Chemistry, vol. 47, pp. 281-286. 2013.
Pre-grant Opposition documents filed for Indian Application No. 201947050111, Apr. 5, 2023, 38 pages.
T. Gao, et al., "Sunscreen Formulas with Multilayer Lamella Structure," Cosmetics & Toiletries, vol. 118, pp. 41-52 (Oct. 2003).
D.Y.M. Leung, et al., "New Insights into Atopic Dermatitis," J. Clin. Invest., vol. 113, pp. 651-657 (2004).
L. Kircik, "Topical Treatment Adherence for Psoriasis," Skin Therapy Letter—Family Practice Edition, vol. 4, No. 2, pp. 4 & 5 (2008).
S.R. Feldman, et al., "Psoriasis: Improving Adherence to Topical Therapy," J. Am. Acad. Dermatol., vol. 59, pp. 1009-1016 (2008).
S.M. Ali, et al., "Skin pH: From Basic Science to Basic Skin Care," Acta Derm. Venereal., vol. 93, pp. 261-267 (1-9), Tbl. SI (2013).
Study NCT01856764, "Topical Roflumilast in Adults with Atopic Dermatitis," sponsored by Takeda, available at https://clinicaltrials.gov/ (Jul. 2015).
Y. Javadzadeh, et al., "Transcutol® (Diethylene Glycol Monoethyl Ether): A Potential Penetration Enhancer," Ch. 12, pp. 195-205, in N. Dragicevic, et al., eds., Percutaneous Penetration Enhancers Chemical Methods in Penetration Enhancement: Modification of the Stratum Corneum (2015).
FDA, Inactive Ingredient Guide (Jan. 1996).
M.J. O'Neil, et al., eds., The Merck Index, pp. 2822, 8379 (15th ed., 2013).
Labeling for ELOCON® (mometasone furoate) Cream (2013).
Labeling for DALIRESP® (roflumilast) Tablets (2013).
Physicians' Desk Reference, pp. 305, 748-52, 1432-35 (67th/2013 ed., 2012).
I.M. Rosenstock, "Understanding and Enhancing Patient Compliance with Diabetic Regimens," Diabetes Care, vol. 8, pp. 610-616 (1985).
J. Urquhart, "The Electronic Medication Event Monitor: Lessons for Pharmacotherapy," Clin. Pharmacokinet., vol. 32, pp. 345-356 (1997).
S.S. Zaghloul, et al., "Objective Assessment of Compliance with Psoriasis Treatment," Arch. Dermatol., vol. 140, pp. 408-414 (2004).
P. Assawasuwannakit, et al., "Quantification of the Forgiveness of Drugs to Imperfect Adherence," CPT Pharmacometrics Syst. Pharmacol., vol. 4, e4, pp. 1-8 (2015).
Notification of Certification of Invalidity, Unenforceability, and/or Non-Infringement for U.S. Pat. Nos. 11,992,480; 12,005,051; 12,005,052; 12,011,437; and 12,016,848 Pursuant to § 505(j)(2)(B)(iv) of the Federal Food, Drug, and Cosmetic Act. (Jul. 16, 2024), 290 pages.

(56) References Cited

OTHER PUBLICATIONS

Bethke et al. (2007) "Dose-Proportional Intraindividual Single and Repeated-Dose Pharmacokinetics of Roflumilast, an Oral, Once-Daily Phosphodiesterase 4 Inhibitor" Journal of Clinical Pharmacology 47:26-36.
Heo et al. (2010) "Topical effects of roflumilast on 1-chloro-2,4-dinitrobenzene-induced atopic dermatitis-like skin lesions in NC/Nga mice" Pharmazie 65:906-12.
Arkema "Oxygenated solvents and derivatives" (2014) 4 pages.
Jin et al. (2012) "Phosphodiesterase 4 and Its Inhibitors in Inflammatory Diseases" Chang Gung Medical Journal 35 (3):197-210.
Pleasants (2018) "Clinical Pharmacology of Oral Maintenance Therapies for Obstructive Lung Diseases" Respiratory Care 63(6):671-89.
Rabe (2011) "Update on roflumilast, a phosphodiesterase 4 inhibitor for the treatment of chronic obstructive pulmonary disease" British Journal of Pharmacology 163:53-67.
Communication of a Notice of Opposition Against European Patent No. 3 684 334, Aug. 20, 2024, 26 pages.
Gattefosse (2015) "Efficient Skin Delivery: No Compromise With Transcutol®" https://api.semanticscholar.org/CorpusID:203610770, 17 pages.
Fenton (2012) "Handbook of Pharmaceutical Excipients" Pharmaceutical Press (7th Ed.), 5 pages.
Osborne (2008) "Review of Changes in Topical Drug Product Classification" Pharmaceutical Technology 32:10, 8 pages.
Aulton (2013) "Aulton's Pharmaceutics" Elsevier Ltd (4th Ed.), 20 pages.
Communication of a Notice of Opposition Against European Patent No. 3 634 380, Sep. 26, 2024, 22 pages.
Felton "Remington: Essentials of Pharmaceutics" London: Pharmaceutical Press (2012), 54 pages.
"Hexylene Glycol GPS Safety Summary," Arkema, Apr. 30, 2012, 5 pages.
Notification of Certification of Invalidity, Unenforceability, and/or Non-Infringement for U.S. Pat. No. 12,042,487 Pursuant to § 505(j)(2)(B)(iv) of the Federal Food, Drug, and Cosmetic Act. (Sep. 12, 2024), 107 pages.
Arkema "Thiochemicals: Sulfur and specialty solutions" (Nov. 24, 2020) 10 pages.
Office Action issued for U.S. Appl. No. 17/821,051 on Jan. 29, 2025, 13 pages.
Office Action issued for U.S. Appl. No. 18/345,760 on Dec. 19, 2024, 43 pages.
Office Action issued for U.S. Appl. No. 17/887,798 on Dec. 19, 2024, 91 pages.
Office Action issued for AU Application No. 2021214399 on Jan. 2, 2025, 4 pages.
Office Action issued for CN Application No. 202180017566.3 on Nov. 1, 2024, 14 pages.

\* cited by examiner

TOPICAL ROFLUMILAST FORMULATION HAVING IMPROVED DELIVERY AND PLASMA HALF-LIFE

This application is a continuation of U.S. Ser. No. 18/353,869, filed Jul. 17, 2023, which is a continuation of U.S. Ser. No. 18/176,601, filed Mar. 1, 2023, now U.S. Pat. No. 11,819,496 issued Nov. 21, 2023, which is a continuation of Ser. No. 17/402,051, filed Aug. 13, 2021, which is a continuation of U.S. Ser. No. 16/778,845, filed Jan. 31, 2020, now U.S. Pat. No. 11,129,818 issued on Sep. 28, 2021, which is a continuation in part of U.S. Ser. No. 16/136,804, filed Sep. 20, 2018, now U.S. Pat. No. 10,940,142 issued Mar. 9, 2021, which is a continuation of U.S. Ser. No. 15/848,505, filed Dec. 20, 2017, now U.S. Pat. No. 10,105,354 issued Oct. 23, 2018, which is a continuation of Ser. No. 15/676,356 filed Aug. 14, 2017, now U.S. Pat. No. 9,884,050 issued Feb. 6, 2018, which is a divisional of U.S. Ser. No. 15/616,409, filed Jun. 7, 2017, now U.S. Pat. No. 9,895,359 issued Feb. 20, 2018, the disclosures of which are incorporated herein in their entirety by reference.

FIELD OF THE INVENTION

The invention pertains to a method for improving the elimination kinetics for topically administered roflumilast. More particularly, the invention pertains to a pharmaceutically acceptable emulsion, suspension, gel, foam or solution formulated to have improved delivery and a longer half-life after topical administration.

BACKGROUND OF INVENTION

Increased adherence to an appropriately prescribed pharmaceutical treatment is associated with better therapeutic outcomes. This axiom of pharmacy was the subject of intense study and quantification after the introduction of antiretroviral (ART) therapy for the treatment of HIV. Determining the factors that negatively impact adherence to ART therapy (Schaecher 2013) was important both to patient care (reduction of morbidity and mortality) and maintaining viral suppression, the key to lessening the risk of HIV transmission. Two factors that strongly affected ARC treatment adherence were: 1) difficulty in following the prescribed treatment and 2) occurrence of treatment related side effects, particularly gastrointestinal adverse events. Although less of a public health concern, treatment adherence by patients suffering from chronic skin disorders, such as psoriasis, have also been studied (Kircik, 2008). Very similar to ART therapy, psoriasis treatment adherence is negatively impacted if the prescribed treatment is difficult to follow because it interferes with daily routines or requires more frequent dosing than once daily. For the topical treatment of psoriasis, adherence rates for a once daily regimen was 82% compared to only a 44% adherence rate for twice daily dosing (Zaghloul, 2004). For chronic skin conditions, adherence with a treatment decreases if the duration of a treatment is long (Rosenstock, 1985). This means that noticeable improvement of the psoriatic plaque (defined as reduction in scale, thickness or inflammation) within the first week of topical application improves treatment adherence compared to a therapy that requires three or four weeks before noticeable clearing of disease.

Adherence linked with treatment implementation is the level of agreement in the patient's actual dosing regimen and the prescribed dosing regimen between initiation and discontinuation of topical therapy. For a psoriasis patient discontinuation of therapy occurs when the plaques completely clear or nearly clear or when a therapy is abandoned due to adverse events or lack of efficacy. Failing to adhere to the prescribed treatment is referred to as adherence imperfection. Adherence imperfection is most often random missed doses which can be denoted as nonconsecutive missed doses or by chance two consecutive missed doses. Three or more consecutive missed doses may be defined as a drug holiday to denote this most severe adherence imperfection. When the patient asks, "What happens if I miss a dose?", the inquiry is referred to as patient concern about adherence imperfection. One of the more common concerns of people taking once daily treatment regimens, compared to twice or four-times daily dosing, is adherence imperfection.

The circumstance of how sensitive therapeutic success is under imperfect adherence is driven by the property known as forgiveness (Urquhart, 1997). A forgiving drug would be one in which therapeutic outcomes are robust to common patterns of imperfect adherence. Forgiveness is a function of the duration of action of the drug substance administered from a specific formulation and the dose interval of the drug product. When the duration of action greatly exceeds the dose interval, then the drug is considered forgiving. The forgiveness index is the number of sequentially missed doses that can occur with a minimal loss of drug effect. The duration of drug effect relates to the pharmacokinetic (PK) and pharmacodynamic (PD) properties inherent to the drug substance and extrinsic PK properties of the drug delivery system.

One factor responsible for the duration of drug effect is the plasma half-life. The plasma concentration of a drug is halved after one half-life. In each succeeding half-life, the plasma concentration is decreased so less drug is eliminated. Thus, after one half-life, 50% of the drug which was absorbed remains in the body; after 2 half-lives, 25% of the drug remains in the body and after 4 half-lives, 6.25% of the drug remains in the body, which is unlikely to have a significant therapeutic effect. The half-life of a drug is critical in determining an appropriate dosing interval. Small improvements in half-life for a short half-life drug can significantly lower the administered dosage. Short half-lives result in high peak to trough ratios and require more frequent dosing. More frequent dosing can result in a poor patient outcome due to a lessening of patient compliance (imperfect adherence).

Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g. bronchitis, asthma, COPD); dermatoses (e.g. proliferative, inflammatory and allergen induced skin disorders), and generalized inflammations in the gastrointestinal region (Crohn's disease and ulcerative colitis).

Roflumilast and its synthesis were described in U.S. Pat. No. 5,712,298 (the "'298 patent"), incorporated herein by reference. Unless otherwise indicated, references incorporated herein by reference are incorporated in their entireties for all purposes. It has long been recognized that pharmaceutical compounds having phosphodiesterase (PDE)-inhibiting properties, such as roflumilast, are useful for treating psoriasis and atopic dermatitis ('298 patent, col 11 lines 52-61) and other chronic inflammatory and allergen-induced dermatoses. For treatment of such dermatoses, roflumilast emulsions, suspensions, gels or solutions for topical application have been described ('298 patent, col 12, lines 37-64).

Although oral tablets of roflumilast have been commercialized, the low aqueous solubility of the compound has been reported to be only 0.53 mg/l at 21° C. in WO95/01338 (corresponding to the '298 patent and incorporated herein by reference in its entirety). This low aqueous solubility has been problematic for the development of parenteral preparations and topical emulsions, suspensions, gels or solutions containing water. In U.S. Pat. No. 9,205,044 (incorporated herein by reference), the poor water solubility of roflumilast was overcome by using an alkoxylated fat, specifically polyoxyethylated 12-hydroxystearic acid, as a co-solvent for parenteral administration. In EP 1511516B1 (corresponding to published U.S. application Ser. No. 14/075,035 incorporated herein by reference), the low water solubility of roflumilast was overcome in topical emulsion (cream) formulations by formulating with polyethylene glycol 400 (PEG 400) in concentrations over 62% (w/w) while keeping water weight percentages under 10%.

Topical application of potent pharmacological agents like roflumilast for treating skin diseases has been found to provide superior delivery, lower systemic exposure and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (API) for application to the skin. To assure consistent delivery of the API into or across the skin, it must remain either: 1) dissolved over the shelf life of the topical product, or 2) suspended as particles having unchanged crystal habit and unchanged particle size distribution over the shelf life of the topical product.

The ability of a dissolved active ingredient to permeate the barrier of the skin is determined by its molecular structure. A well-known relationship between molecular structure and skin penetration is that increasing molecular weight decreases the rate that an active crosses the skin (J D Bos, M M Meinardi, Exp Dermatol. 2000 June; 9(3):165-9). Another well-understood relationship is that increasing the octanol-water partition coefficient of a hydrophilic active initially increases the rate that an active permeates the skin, but then decreases skin permeation once the active becomes too lipophilic to partition out of the stratum corneum and into the lower layers of the epidermis (D. W. Osborne and W. J. Lambert, Prodrugs for Dermal Delivery, K. B. Sloane ed., Marcel Dekker, New York 163-178 (1992)). The optimal octanol-water partition coefficient is usually at log P values of 2-3. The rate that an active ingredient crosses into the viable epidermis can be further modified based on the composition of the topical product. Final pH of the formulation may be critical, because dissolved ionized active ingredients typically do not permeate the skin as effectively as active ingredients that do not carry a charge (N. Li, X. Wu, W. Jia, M. C. Zhang, F. Tan, and J Zhang. *Drug Dev Indust Pharm* 38(8)985-994). Functional ingredients such as skin penetration enhancers (D. W. Osborne and J. J. Henke, Pharmaceutical Technology 21(11)58-66(1997)) can be added to the topical product to increase skin permeation. For a dissolved active in the topical product, the closer the drug concentration is to the amount of active required to saturate the drug product, the greater the thermodynamic driving force of the active to cross the skin, i.e. the greater the skin flux of the active. The scientific literature guides formulators on how to increase penetration through the polar route, the nonpolar route, and the intercellular lipid pathway or transfollicular penetration. While these theories and mechanisms are sometimes conflicting, it is generally accepted that the most consistent skin permeation of a drug from a topical product occurs when the active ingredient is dissolved in the formulation. For this reason, formulators generally avoid developing a topical product that will have particles or crystals of the active ingredient precipitate during storage according to labeled storage instructions. Precipitation of the active ingredient can occur for various reasons. Particular active ingredients, when formulated with particular pharmaceutical excipients will tend to form supersaturated solutions. At the time of manufacture, all of the active ingredient will be in solution. After days, weeks, or months, this metastable topical product will equilibrate and active ingredient particles will form. If a topical product contains a volatile solvent such as ethanol, then evaporation of the solvent upon storage could result in precipitation of the active ingredient. A less soluble polymorph (Pudipeddi and Serajuddin, J. Pharm. Sci., 94(5) 929-939 (2005)) may nucleate in the topical product and form active ingredient particles that will not re-dissolve. Other products may be formulated too close to the saturation limit of the active ingredient with the result that minor shifts in storage temperatures will cause precipitation. It should be noted that the dramatic temperature shifts that can occur during shipping are expected to cause the reversible precipitation of the active ingredient. Regardless of the reason, irreversible precipitation of the active ingredient during storage of a topical product can have profound effects on the bioavailability and efficacy of a topical product, since only dissolved active ingredients can penetrate into intact stratum corneum, the outermost layer of epithelium of the skin.

For a suspended active ingredient, properties in addition to molecular structure influence skin permeation. The ratio of dissolved to suspended active ingredient can have a significant influence on the amount of active delivered after topical application. It has been shown that optimal drug delivery can be achieved for particular drugs and particular diseases by utilizing a topical composition that includes a dissolved active ingredient that has the capacity to permeate the stratum corneum layer of the epidermis and become available systemically, along with an active ingredient in a microparticulate state that does not readily cross the stratum corneum of the epidermis (U.S. Pat. No. 5,863,560 hereby incorporated by reference). Another property of a suspended active ingredient that affects its delivery is the distribution of suspended particle size. It has been shown that a 6 micron particle will target the hair follicle and penetrate to a depth of 500 micrometers in a terminal hair. For a suspended particle of 0.75 microns to 1.5 microns in size, the particle penetrates the terminal hair shaft to a depth of 800 micrometers (A Patzelt, F Knorr, U Blume-Peytavi, W Sterry, J Lademann, Drug Discovery Today: Disease Mechanisms, 5(2)2008 pages e173-e181). Thus, for suspended active ingredients, skin permeability depends on the following properties: 1) molecular structure of dissolved active ingredient, 2) particulate/crystalline structure of the suspended active ingredient, 3) particle size of the suspended active ingredient, and 4) particle size distribution of the suspended active ingredient. The ability of a topical product composition to modify the skin permeation is similar for suspended active ingredients and dissolved active ingredients. Because skin permeability is dependent upon additional properties of the suspended active ingredients, consistent delivery from topical products containing suspended actives is more difficult to maintain than for topical products containing only dissolved active ingredients.

Consistent delivery of a suspended active ingredient from a topical product is assured by formulation into a product in which the suspended particles do not significantly change in size or amount over the shelf life of the product. Change over time in the ratio of dissolved active ingredient to particulate active ingredient can dramatically change the skin permeation of the active ingredient. The same mechanisms described above (supersaturation, temperature changes, evaporation, polymorphic transformation) that can cause precipitation of dissolved active ingredients can alter the dissolved-to-particulate ratio for suspended active ingredients. Change over time in the particle size or particle size distribution of the dispersed active ingredient can also dramatically change the skin permeation of the active ingredient. Sometimes this change in particle size or particle size distribution can be explained by Ostwald ripening of the particles. Ostwald ripening occurs when small particles in the topical product dissolve and redeposit onto larger particles suspended in the same container of topical product. Over time this phenomenon shifts the particle size distribution toward larger particles at the expense of the smaller particles. Ostwald ripening and precipitation of a less soluble polymorph are two major problems in developing topical products containing suspended actives.

In addition to the consistent delivery of a suspended active ingredient from a topical product, successful treatment also depends on the elimination kinetics of the active ingredient. After a drug is absorbed into a patient's body, elimination begins thereby reducing the concentration over time. The half-life determines the length of time that the drug will be effective. When administering multiple 0.375 mg doses of immediate release oral roflumilast (Huang, 2018), the mean plasma half-life of the drug was found to be about 1 day (mean value of 12-subjects was 25.6 hours with a standard deviation of 8.5 hours). Since the maximum plasma concentration (11.4 ng roflumilast per mL plasma) occurs for roflumilast about 1 hour after oral dosing, mean plasma concentration at the time of the first missed dose (1 day after the most recent dose) will be approximately 5.7 ng/mL (half the 11.4 ng/mL maximum plasma concentration). If two consecutive doses are missed, then the roflumilast plasma concentration will be about 2.8 ng/mL two days after the most recent dose and about 1.4 ng/mL just prior to a return to treatment adherence, i.e. the patient does not miss a third consecutive dose, and taking a tablet 72 hours after the most recent oral dose of roflumilast. If the half-life of roflumilast could be increased so that systemic plasma levels of roflumilast did not decrease to half each day that a dose is missed, then the forgiveness index for the drug delivery system would be increased. For oral roflumilast, use of a sustained release oral drug delivery system instead of the immediate release tablet studied by Huang, would be an example of extrinsic PK property modification to increase the adherence imperfection forgiveness of the product that would benefit the patient that missed one or more doses of roflumilast.

When topically treating a chronic skin condition such as psoriasis, the treatment adherence benefit of developing a product having once daily dosing is offset by increased concern about adherence imperfection for patients applying once daily topicals. Even roflumilast, a pharmaceutical active having a one-day oral half-life due to intrinsic PK/PD properties, would benefit from a topical sustained release formulation that significantly increases the duration of effect, i.e. increases the plasma half-life for topical roflumilast.

A topical roflumilast formulation with a longer half-life and consistent delivery would be advantageous. It would be advantageous to develop and provide a pharmaceutical formulation containing roflumilast that after multiple topical applications could maintain consistent delivery and therapeutically effective dose levels despite adherence imperfections such as one, two or more consecutive days of missed dosing.

SUMMARY OF THE INVENTION

In accordance with the present invention, it has been discovered that hexylene glycol inhibits crystalline growth of suspended or precipitated roflumilast particles in formulations containing pharmaceutically acceptable solvents and thus results in consistent delivery with topically applied formulations due to better skin permeability. In addition, the inclusion of a solvent and phosphate ester surfactant blend of dicetyl phosphate and ceteth-10 phosphate in a topical formulation containing roflumilast increases the plasma half-life and the duration of effect. The increased half-life and duration of effect removes the concern that adherence imperfection will decrease therapeutic success and increases the adherence imperfection forgiveness of topically applied roflumilast.

BRIEF DESCRIPTION OF THE DRAWINGS

FIG. 11a shows Sample 36-1 roflumilast particles precipitated in a cream composition with diethylene glycol monoethyl ether (DEGEE) and without hexylene glycol. The three largest roflumilast particles were measured (0.07 mm×0.09 mm; 0.06 mm×0.06 mm; and 0.10 mm×0.05 mm) and found to have a mean surface area of 5,000 square microns. FIG. 11b shows Sample 36-2 roflumilast particles precipitated in a cream composition with both diethylene glycol monoethyl ether (DEGEE) and hexylene glycol. The three largest roflumilast particles were measured (0.05 mm×0.03 mm; 0.05 mm×0.03 mm and 0.05 mm×0.03 mm) and found to have a mean surface area of 1,500 square microns.

DETAILED DESCRIPTION OF THE INVENTION

Figure 1:
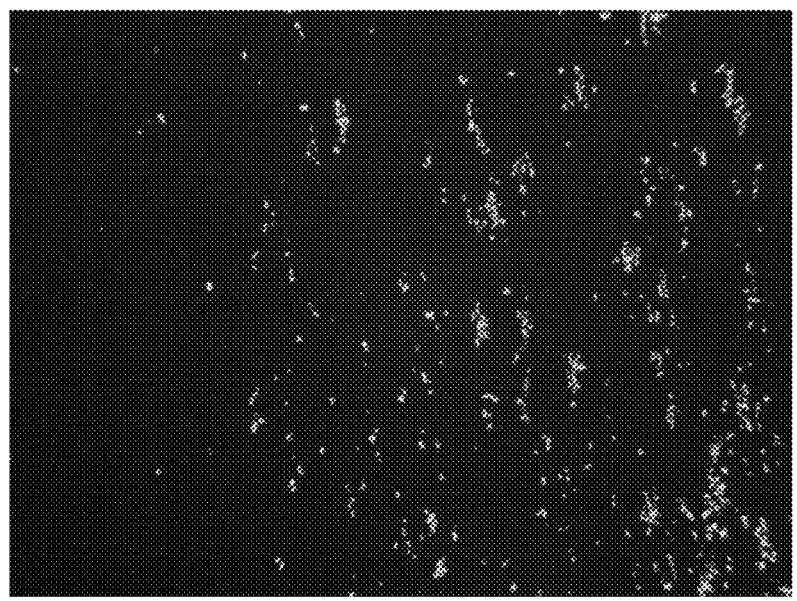
FIG. 1 shows Sample 19-2 "dry" roflumilast crystals from ferrer-Interquim S.A. Batch A14367P, the drug substance used in all the examples in this specification. The roflumilast crystals are 0.01 mm-0.02 mm in length.

Roflumilast is a compound of the formula (I)

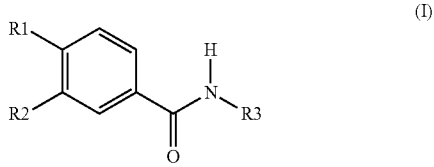

wherein R1 is difluoromethoxy, R2 is cyclopropylmethoxy and R3 is 3,5-dichloropyrid-4-yl.

This compound has the chemical name N-(3,5-dichloropyrid-4-yl)-3-cyclopropylmethoxy-4-difluoromethoxybenzamide (INN: roflumilast).

Hexylene glycol (PharmaGrade. USP/NF) is 2-methyl-2,4-pentanediol of the formula (II).

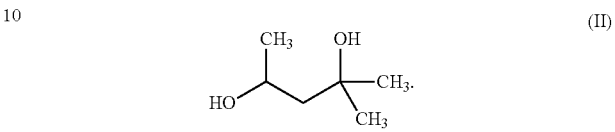

The emulsifier blend of cetearyl alcohol (CAS 67762 30 0), dicetyl phosphate (CAS 2197 63 9) and ceteth-10 phosphate (CAS 50643-20-4) is manufactured by Croda under the tradename CRODAFOS™ CES. This commercially available emulsifier blend is a self-emulsifying wax that is predominately the waxy material cetearyl alcohol (which is a mixture cetyl alcohol ($C_{16}H_{34}O$) and stearyl alcohol ($C_{18}H_{38}O$)) combined with 10-20% dicetyl phosphate and 10-20% ceteth-10 phosphate. Self-emulsifying waxes form an emulsion when blended with water. When CRODAFOS™ CES is added to water it spontaneously forms an emulsion having a pH of about 3. Sodium hydroxide solution is added to increase the pH to the desired value.

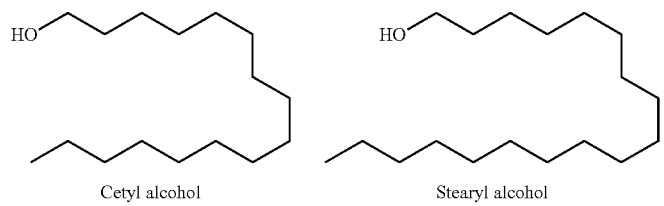

Cetyl alcohol    Stearyl alcohol

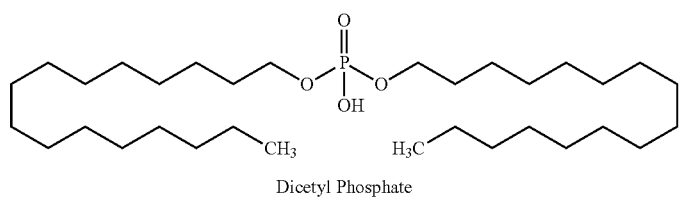

Dicetyl Phosphate

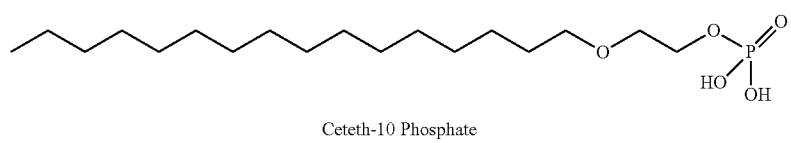

Ceteth-10 Phosphate

The present invention is directed to the addition of hexylene glycol, a solvent and/or a phosphate ester surfactant blend of dicetyl phosphate and ceteth-10 phosphate to a roflumilast-containing pharmaceutical composition that contains a pharmaceutically acceptable solvent, including water, to inhibit growth of roflumilast crystals in the composition and/or to extend the half-life of roflumilast in a patient's body after administration.

For topical products designed to contain suspended roflumilast particles or crystals, the addition of hexylene glycol to a composition containing roflumilast, will inhibit (i.e., prevent or substantially reduce in comparison to compositions that do not contain a hexylene glycol) changes in particle size distribution over the shelf life of the product and assure consistent bioavailability. For topical products designed to have roflumilast completely dissolved, hexylene glycol inhibits the growth of precipitated roflumilast particles.

Drug products that have fully dissolved drug substance for the labeled storage conditions over product shelf life will have the active precipitate if the product is formulated to maintain significant thermodynamic driving force. Typical storage conditions for a topical pharmaceutical cream are: Store at room temperature: 60° F./15° C.-80° F./26° C. Do not freeze. It is understood by product development scientists and regulatory agency reviewers that a topical product will not always be stored over this temperature range. Therefore, the FDA requires that all topical products undergo freeze-thaw cycling and temperature excursion studies. The active is neither required nor expected to remain in solution when the product is exposed to temperatures of −20° C., dramatically below 15° C. (60° F.) of the labeled storage condition. Since topical products containing completely dissolved drug are usually formulated near saturation, i.e. near maximum thermodynamic driving force, most topical products experience precipitation of the active ingredient during freeze-thaw cycling or temperature excursion studies. The addition of hexylene glycol prevents crystal growth of roflumilast when precipitation occurs due to temperature excursions below the labeled storage conditions. Inhibiting crystal growth assures that any precipitated active will quickly return to being completely dissolved once the product is returned to controlled room temperature. The prompt return of the precipitated roflumilast to a fully dissolved state assures consistent, reproducible bioavailability, efficacy and safety of the topically applied product. Hexylene glycol can be added between 0.1% and 20% on a weight/weight basis, preferably between 0.25% and 8% on a weight/weight basis and most preferably between 0.5% and 2% on a weight/weight basis.

In order to extend the half-life of roflumilast in a patient's body after administration, a self-emulsifying wax blend of dicetyl phosphate and ceteth-10 phosphate and a solvent is included in the formulation. The plasma half-life of roflumilast after intravenous administration in humans is about 15 hours; after oral administration the plasma half-life is about 17-30 hours (see Bethke et al., High Absolute Bioavailability of the New Oral Phosphodiesterase-4 Inhibitor Roflumilast, International Journal of Clinical Pharmacology and Therapeutics, vol. 49, No. 1, 2011, pp. 51-57). The plasma half-life of roflumilast after topical administration of a formulation comprising a self-emulsifying wax blend of dicetyl phosphate and ceteth-10 phosphate and a solvent is 3.4-3.7 days (about 81-89 hours).

The topical roflumilast product formulations that benefit from the addition of hexylene glycol, a self-emulsifying wax blend of dicetyl phosphate and ceteth-10 phosphate and/or a solvent include but are not limited to aerosols, foams, sprays, emulsions (which can also be called creams, lotions, or ointments), gels (two phase or single phase), liquids, ointments, pastes, shampoos, suspensions, and systems. These are the tier two terms within compendia taxonomy for dosage forms containing pharmaceutical active ingredients (US Pharmacopeia <1151>).

The roflumilast formulations can be prepared by methods known in the art (e.g. see the '298 patent and U.S. application Ser. No. 14/075,035).

Preferably, hexylene glycol, a self-emulsifying wax blend of dicetyl phosphate and ceteth-10 phosphate, and/or a solvent is added to compositions containing 0.005-2.0% roflumilast that may be in one of the following forms:

An oil-in-water emulsion: The product may be a formulation in which hexylene glycol, a self-emulsifying wax blend of dicetyl phosphate and ceteth-10 phosphate, and/or a solvent is added to an emulsion comprising a discrete phase of a hydrophobic component and a continuous aqueous phase that includes water and optionally one or more polar hydrophilic excipients as well as additional solvents, co-solvents, salts, surfactants, emulsifiers, and other components. These emulsions may include water-soluble or water-swellable polymers that help to stabilize the emulsion. Preferably, the emulsifier is a self-emulsifying wax blend of dicetyl phosphate and ceteth-10 phosphate.

Thickened Aqueous gels: These systems include an aqueous phase which has been thickened by suitable natural, modified natural, or synthetic thickeners such as described below. Alternatively, the thickened aqueous gels can be thickened using suitable polyethoxylate alky chain surfactants or other nonionic, cationic, or anionic systems.

Thickened Hydroalcoholic gels: These systems include a blend of water and alcohol as the polar phase which has been thickened by suitable natural, modified natural, or synthetic polymers such as described below. Alternatively, the thickened hydroalcoholic gels can be thickened using suitable polyethoxylate alky chain surfactants or other nonionic, cationic, or anionic systems. The alcohol can be ethanol, isopropyl alcohol or other pharmaceutically acceptable alcohol.

Hydrophilic gels: These are systems in which the continuous phase includes at least one water soluble or water dispersible hydrophilic component other than water. The formulations may optionally also contain water up to 60% by weight. Higher levels may be suitable in some compositions. Suitable hydrophilic components include one or more glycols such as polyols such as glycerin, propylene glycol, butylene glycols, polyethylene glycols (PEG), random or block copolymers of ethylene oxide, propylene oxide, and/or butylene oxide, polyalkoxylated surfactants having one or more hydrophobic moieties per molecule, silicone copolyols, blend of ceteareth-6 and stearyl alcohol as well as combinations thereof, and the like.

A water-in-oil emulsion: The compositions may be formulations in which roflumilast is incorporated into an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) that help to stabilize the emulsion. Preferably, the emulsifier is a self-emulsifying wax blend of dicetyl phosphate and ceteth-10 phosphate.

A hydrophilic or hydrophobic ointment: The compositions are formulated with a hydrophobic base (e.g. petrolatum, thickened or gelled water insoluble oils, and the like)

and optionally having a minor amount of a water soluble phase. Hydrophilic ointments generally contain one or more surfactants or wetting agents Solvents Compositions according to the present invention may include one or more solvents or co-solvents to obtain the desired level of active ingredient solubility in the topical product. The solvent may also modify skin permeation or the activity of other excipients contained in the formulation. Solvents include but are not limited to acetone, ethanol, benzyl alcohol, butyl alcohol, diethyl sebacate, diethylene glycol monoethyl ether, diisopropyl adipate, dimethyl sulfoxide, ethyl acetate, isopropyl alcohol, isopropyl isostearate, isopropyl myristate, N-methyl pyrrolidinone, polyethylene glycol, glycerol, propylene glycol and SD alcohol.

Moisturizers

Compositions according to the present invention may include a moisturizer to increase the level of hydration. The moisturizer can be a hydrophilic material including humectants or it can be a hydrophobic material including emollients. Suitable moisturizers include but are not limited to:1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, and stearyl alcohol.

Surfactants and Emulsifiers

Compositions according to the present invention optionally can include one or more surfactants to emulsify the composition and to help wet the surface of the actives or excipients. As used herein the term "surfactant" means an amphiphile (a molecule possessing both polar and nonpolar regions which are covalently bound) capable of reducing the surface tension of water and/or the interfacial tension between water and an immiscible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ceteareth-20, cetearyl ethylhexanoate, ceteth-10, ceteth-2, ceteth-20, ceteth-23, choleth-24, cocamide ether sulfate, cocamine oxide, coco betaine, coco diethanolamide, coco monoethanolamide, coco-caprylate/caprate, disodium cocoamphodiacetate, disodium laureth sulfosuccinate, disodium lauryl sulfoacetate, disodium lauryl sulfosuccinate, disodium oleamide monoethanolamine sulfosuccinate, docusate sodium, laureth-2, laureth-23, laureth-4, lauric diethanolamide, lecithin, methoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesquistearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGEN™ 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax. Preferably, the emulsifier is a self-emulsifying wax blend of dicetyl phosphate and ceteth-10 phosphate.

Polymers and Thickeners

For certain applications, it may be desirable to formulate a product that is thickened with soluble, swellable, or insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, carboxy vinyl copolymer, carboxymethylcellulose, carboxypolymethylene, carrageenan, guar gum, hydroxyethyl cellulose, hydroxypropyl cellulose, microcrystalline wax, and methylcellulose, Additional Components Compositions according to the present invention may be formulated with additional components such as fillers, carriers and excipients conventionally found in cosmetic and pharmaceutical topical products. Additional components including but not limited to antifoaming agents, preservatives (e.g. p-hydroxybenzoic esters, benzyl alcohol, phenylmercury salts, chlorocresol), antioxidants, sequestering agents, stabilizers, buffers, pH adjusting solutions, skin penetration enhancers, film formers, dyes, pigments, diluents, bulking agents, fragrances and other excipients to improve the stability or aesthetics, may be added to the composition.

Compositions according to the present invention may be formulated with additional active agents depending on the condition being treated. The additional active agents include but are not limited to NSAIDs (e.g. Aspirin, Ibuprofen, Ketoprofen, Naproxen), Apremilast, JAK inhibitors (e.g. Tofacitinib, Ruxolitinib, Oclacit), leukotriene inhibitors (e.g. Zileuton, Zafirlukast, Montelukast), mast cell stabilizers (e.g. Nedocromil, Cromolyn sodium, Ketotifen, Pemirolast), Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthiouracil, 6-thioguanine, Sulfasalazine, Mycophenolate mofetil, Fumaric acid esters, Corticosteroids (e.g. Aclometasone, Amcinonide, Betamethasone, Clobetasol, Clocortolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, bronchodialators (e.g. beta-agonists, anticholinergics, theophylline), and antibiotics (e.g. erythromycin, ciprofloxacin, metronidazole).

Administration and Dosage

The compositions according to the present invention can be administered by any suitable administration route including but not limited to oral, rectal, parenteral (e.g. intradermal, subcutaneous, intramuscular, intravenous, intramedullary, intra arterial, intrathecal, epidural), ocular, inhalation, nebulization, cutaneously (topically), transdermally, and mucosally (e.g. sublingual, buccal, nasally). In a preferred embodiment, the composition is administered topically.

Suitable pharmaceutical dosage forms include but are not limited to emulsions, suspensions, sprays, oils, ointments, fatty ointments, creams, pastes, gels, foams transdermal patches and solutions (e.g. injectable, oral).

The composition preferably contains roflumilast, salts of roflumilast, the N-oxide of roflumilast or salts thereof in an amount of 0.005-2% w/w, more preferably 0.05-1% w/w, and most preferably 0.1-0.5% w/w per dosage unit.

The composition preferably contains hexylene glycol in an amount of between 0.1% and 20% w/w, more preferably between 0.25% and 8% w/w and most preferably between 0.5% and 2% w/w.

The composition preferably contains a phosphate ester surfactant in the formulation which is in an amount sufficient to produce a stable emulsion having uniform globule size. The concentration of the phosphate ester surfactant generally may be any concentration between 1.0% to 25% w/w. The preferred concentration can be different for different administration forms. In a preferred embodiment, when the formulation is a cream or ointment, the concentration of the phosphate ester surfactant is between 2.5% and 20%, with a more preferred concentration range between 5% and 15%, and a most preferred concentration being about 10% w/w. When the formulation is in the form of a foam, the concentration is preferably between 1.0%-10%, more preferably between 1.0%-10%, and most preferably 2%. Preferably the phosphate ester surfactant is provided in a self-emulsifying wax blend of dicetyl phosphate and ceteth-10 phosphate.

The composition preferably contains a solvent in an amount sufficient to obtain the desired level of active ingredient solubility in the formulation. The solvent is preferably is in an amount of 10-30% (w/w). The ratio of solvent to water is preferably from 1:10 to 20:1. Preferably, the solvent is diethylene glycol monoethyl ether (DEGEE).

The topical formulation containing roflumilast, is applied to the skin in an amount that is sufficient to obtain the desired pharmacologic effect, which typically is to ameliorate the signs and/or symptoms of a medical disorder. The amount of the formulation that is applied may vary depending on the amount of roflumilast that is contained within the formulation, the concentration of the roflumilast within the formulation, and the frequency in which the formulation is intended to be applied. Generally, the formulation is applied with a frequency between weekly to several times daily, preferably between every other day to three times daily, and most preferably one or two times daily.

The composition can be used in veterinary and in human medicine for the treatment and prevention of all diseases regarded as treatable or preventable by using roflumilast, including but not limited to acute and chronic airway disorders such as bronchitis, allergic bronchitis, asthma, and COPD; proliferative, inflammatory and allergic dermatoses such as psoriasis, scalp psoriasis, or inverse psoriasis, irritant and allergic contact eczema, hand eczema, atopic dermatitis, seborrheic dermatitis, lichen simplex, sunburn, aphthous ulcers, lichen planus, vitiligo, pruritus in the genital or anal regions, alopecia areata, hypertrophic scars, discoid lupus erythematosus, follicular and extensive pyodermas, endogenous and exogenous acne, acne rosacea, disorders which are based on an excessive release of TNF and leukotrienes, disorders of the heart which can be treated by PDE inhibitors, inflammations in the gastrointestinal system or central nervous system, disorders of the eye, disorders which can be treated by the tissue-relaxant action of PDE inhibitors and other proliferative, inflammatory and allergic skin disorders; and immune mediated diseases such as arthritis including rheumatoid arthritis, rheumatoid spondylitis, osteoarthritis, and psoriatic arthritis. Preferably, the composition is used to treat proliferative, inflammatory and allergic dermatoses such as psoriasis (vulgaris), eczema, acne, Lichen simplex, sunburn, pruritus, alopecia areata, hypertrophic scars, discoid lupus erythematosus, and pyodermas.

The composition can include additional active agents suitable for treating the patient's condition. For example, when proliferative, inflammatory and allergic dermatoses are treated, the composition may additionally include Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthiouracil, 6-thioguanine, Sulfasalazine, Mycophenolate mofetil, Fumaric acid esters, Corticosteroids (e.g. Aclometasone, Amcinonide, Betamethasone, Clobetasol, Clocortolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, Adalimumab, Ustekinumab, Infliximab, and/or antibiotics.

The formulation for topical application containing roflumilast, may be prepared by processes typically used in the field of manufacture of pharmaceutical formulations for topical application. In order to make a single-phase formulation, such as a liquid, the constituents of the formulation may be combined and mixed until a homogenous solution or suspension of the active ingredient is obtained. In order to make a multiphase formulation such as an emulsion, for example, the components of the aqueous phase and of the oil phase may be separately combined and mixed until homogenous solutions are obtained and then the aqueous solution and the oil solution may be combined and mixed, such as by shear mixing, to form the formulation. The one or more drug actives may be dissolved (molecularly dispersed), complexed, or associated with an excipient or other active, or may be particulate (amorphous or crystalline). The oil phase may be added to the water phase, or the water phase may be added to the oil phase. The phases may be combined and mixed, such as at elevated temperatures of 50-90° C. or at room temperature, that is between 20-30° C., or at a temperature between room temperature and the elevated temperatures.

The following examples are provided to enable those of ordinary skill in the art to make and use the methods and compositions of the invention. These examples are not intended to limit the scope of what the inventors regard as their invention. Additional advantages and modifications will be readily apparent to those skilled in the art.

Example 1

A few mg of roflumilast API (Batch A14367P from Interquim S.A.) dry powder was tapped onto a microscope slide, a coverslip was moved into place and crystal habit and particle size of the API was examined using polarized light microscopy using a 10× objective (FIG. 1, microscope sample 19-2).

Figure 2:
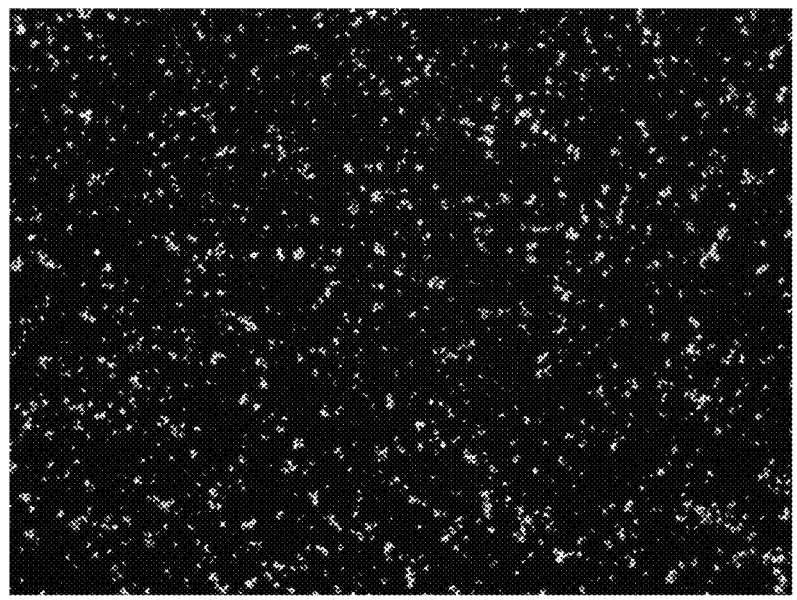
FIG. 2 shows Sample 20-3 roflumilast crystals suspended in equimolar hexylene glycol:water solution after storage for six weeks at room temperature under 10× power. The roflumilast crystals are 0.01 mm-0.02 mm in length.
Figure 3:
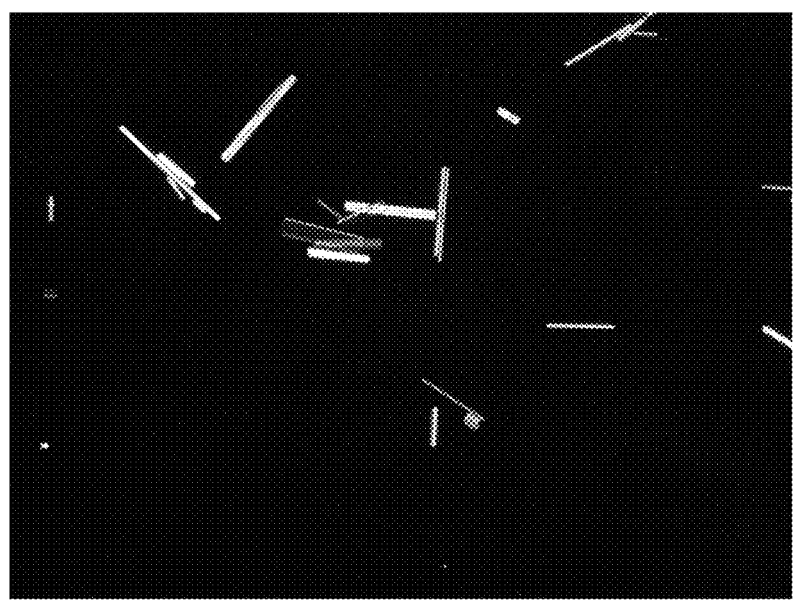
FIG. 3 shows Sample 20-2 roflumilast crystals suspended in equimolar diethylene glycol monoethyl ether:water solution after storage for six weeks at room temperature. The roflumilast crystals are 0.04 mm-0.20 mm in length and 0.01 mm-0.02 mm in width.

0.0092 grams of roflumilast (Batch A14367P from Interquim S.A.) was weighed into a liquid scintillation vial. An equimolar blend of hexylene glycol (lot 1AC0818, Spectrum) and distilled water was added dropwise with mixing to the vial containing roflumilast to produce a suspension of roflumilast in excess of the solubility limit. An equimolar blend is 86.7% hexylene glycol and 13.3% water on a weight/weight percent basis. After mixing each addition of hexylene glycol:water blend, the tightly capped vial was returned to a water bath set at 25° C. It required 0.7962 grams of equimolar Hexylene Glycol:Water blend to completely dissolve the 0.0092 grams of roflumilast and give a 1.14% roflumilast in equimolar Hexylene Glycol:Water (wt/wt %) solution. 0.0064 grams of roflumilast was added to this sample (labeled 12-3) to form a finely dispersed suspension at 25° C. and the vial was then stored undisturbed at about 15-18° C., protected from the light for six weeks. A sample of the roflumilast crystals was removed from the vial, placed on a microscope slide (with coverslip) and then examined using polarized light microscopy using a 10× objective (FIG. 2, microscope sample 20-3). 0.0111 grams of roflumilast (Batch A14367P from Interquim S.A.) was weighed into a liquid scintillation vial. An equimolar blend of diethylene glycol (DEGEE) (Transcutol P, lot 146063, Gattefosse) and distilled water was added dropwise with mixing to the vial containing roflumilast to produce a suspension of roflumilast in excess of the solubility limit. An equimolar blend is 88.3% DEGEE and 11.7% water on a weight/weight percent basis. After mixing each addition of DEGEE:water blend, the tightly capped vial was returned to a water bath set at 25° C. It required 0.2477 grams of equimolar DEGEE:Water blend to completely dissolve the 0.0111 grams of roflumilast and give a 4.29% roflumilast in equimolar DEGEE:Water (wt/wt %) solution. This sample (labeled 13-1) was a solution of roflumilast at 25° C. and the vial was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 10× objective (FIG. 3, microscope sample 20-2).

Example 2

Figure 4:
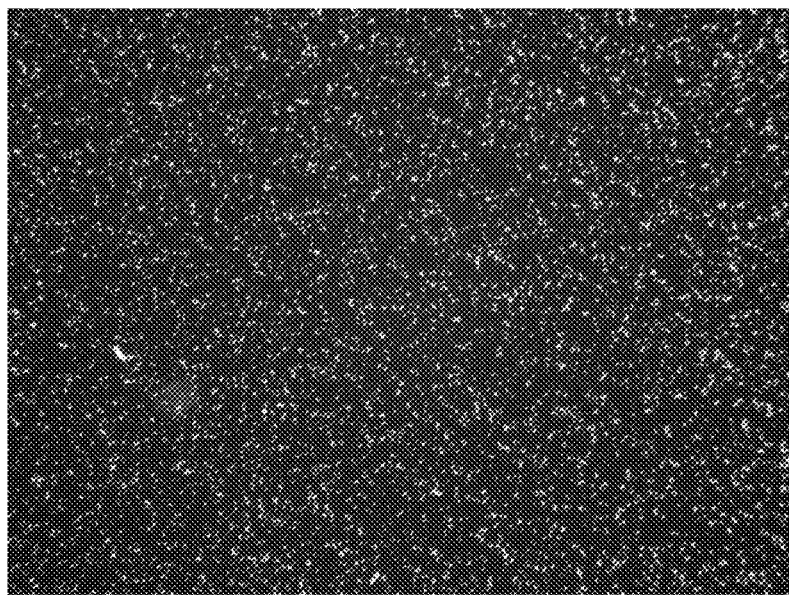
FIG. 4 shows Sample 20-3 roflumilast crystals suspended in equimolar hexylene glycol:water solution after storage for six weeks at room temperature under 4× power. The roflumilast crystals are 0.01 mm-0.02 mm in length.
Figure 5:
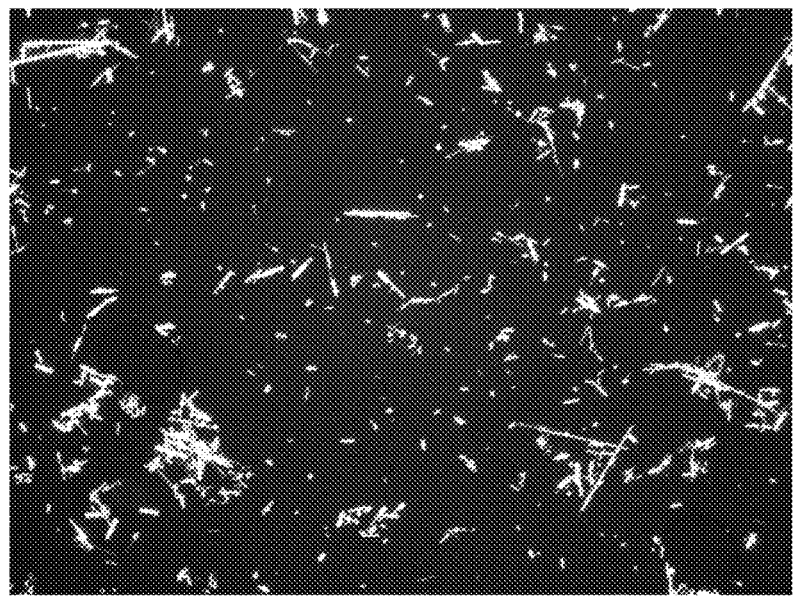
FIG. 5 shows Sample 21-2 roflumilast crystals suspended in equimolar ethanol:water solution after storage for six weeks at room temperature. The roflumilast crystals are 0.05 mm-0.25 mm in length and 0.02 mm in width.

0.0092 grams of roflumilast (Batch A14367P from Interquim S.A.) was weighed into a liquid scintillation vial. An equimolar blend of hexylene glycol (lot 1AC0818, Spectrum) and distilled water was added dropwise with mixing to the vial containing roflumilast to produce a suspension of roflumilast in excess of the solubility limit. An equimolar blend is 86.7% hexylene glycol and 13.3% water on a weight/weight percent basis. After mixing each addition of hexylene glycol:water blend, the tightly capped vial was returned to a water bath set at 25° C. It required 0.7962 grams of equimolar Hexylene Glycol:Water blend to completely dissolve the 0.0092 grams of roflumilast and give a 1.14% roflumilast in equimolar Hexylene Glycol:Water (wt/wt %) solution. 0.0064 grams of roflumilast was added to this sample (labeled 12-3) to form a finely dispersed suspension at 25° C. and the vial was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 4, microscope sample 20-3).
0.0260 grams of roflumilast (Batch A14367P from Interquim S.A.) was weighed into a liquid scintillation vial. 1.0705 grams of an ethanol:water blend (Everclear which is 74.98% ethanol and 25.02% water on a weight/weight percent basis or 95% alcohol by volume) was added to produce a dispersion of roflumilast in an ethanol:water blend in excess of the solubility limit. This sample (labeled as "Alc") was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 5, microscope sample 20-3).

Figure 6:
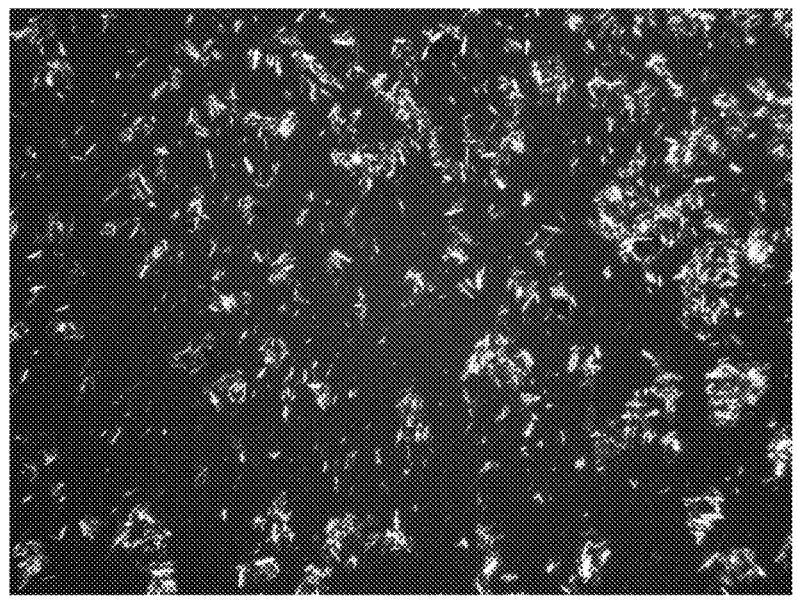
FIG. 6 shows Sample 21-3 roflumilast crystals suspended in equimolar PEG 400:water solution after storage for six weeks at room temperature. The roflumilast crystals are 0.05 mm-0.07 mm in length and 0.02 mm in width.

0.0180 grams of roflumilast (Batch A14367P from Interquim S.A.) was weighed into a liquid scintillation vial. Polyethylene glycol 400 (lot 1 DE0880, Spectrum) was added dropwise with mixing to the vial containing roflumilast to produce a suspension of roflumilast in excess of the solubility limit. After mixing each addition of polyethylene glycol 400, the tightly capped vial was returned to a water bath set at 25° C. It required 0.5486 grams of propylene glycol 400 to completely dissolve the 0.0180 grams of roflumilast and give a 3.18% roflumilast in polyethylene glycol 400 solution. This sample (labeled as "PEG 400") was a solution at 25° C. and was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 4× objective (FIG. 6, microscope sample 21-3).

Figure 7:
FIG. 7 shows Sample 21-4 roflumilast crystals suspended in equimolar DMSO:water solution after storage for six weeks at room temperature. The roflumilast crystals are 0.10 mm-0.67 mm in length and 0.02 mm-0.10 mm in width.

0.0103 grams of roflumilast (Batch A14367P from Interquim S.A.) was weighed into a liquid scintillation vial and mixed with 0.2501 grams of dimethyl sulfoxide (lot US150, Gaylord Chemical) to give a 28.5% solution of roflumilast at 25° C. This sample (labeled as "DMSO") was then stored undisturbed at about 15-18° C., protected from the light for six weeks. A sample of precipitated the roflumilast crystals was removed from the vial, placed on a microscope slide (with coverslip) and then examined using polarized light microscopy using a 4× objective (FIG. 7, microscope sample 21-4).

Figure 8:
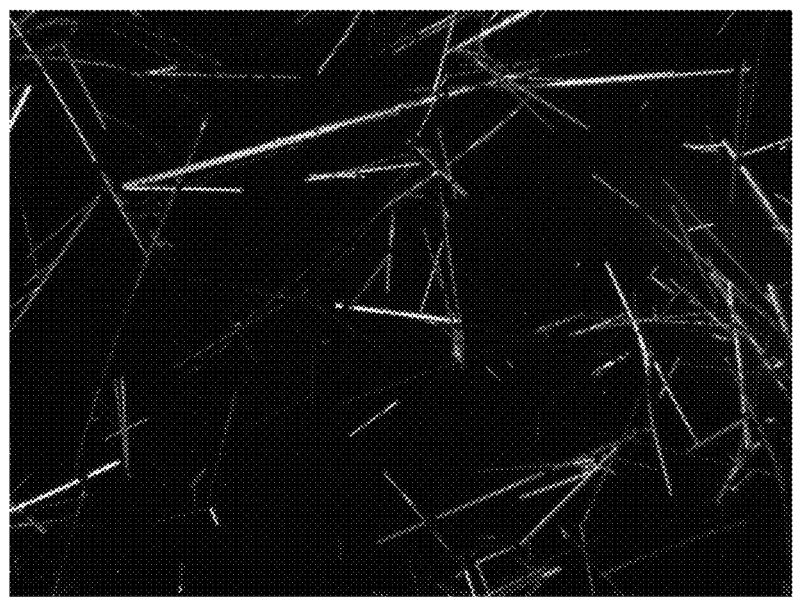
FIG. 8 shows Sample 21-5 roflumilast crystals suspended in equimolar propylene glycol:water solution after storage for six weeks at room temperature. The roflumilast crystals are 0.20 mm-1.60 mm in length and 0.02 mm in width.

0.0061 grams of roflumilast (Batch A14367P from Interquim S.A.), 1.9332 grams of propylene glycol (lot 1 EC0004, Spectrum) and 0.2335 grams distilled water was mixed to initially form a clear solution at 25° C. The composition of the sample was 0.28% roflumilast, 88.97% propylene glycol and 10.75% water on a weight/weight % basis. After 105 minutes of storage at 25° C. a "dusting" of fine roflumilast crystals were observed on the bottom of the vial. Six days later additional crystals had settled to the bottom of the vial. This sample (labeled 7-2) was then stored undisturbed at about 15-18° C., protected from the light for six weeks. A sample of precipitated roflumilast crystals was removed from the vial, placed on a microscope slide (with coverslip) and then examined using polarized light microscopy using a 4× objective (FIG. 8, microscope sample 21-5).

Example 3

Dramatically greater roflumilast crystalline growth was observed in an equimolar N-methyl pyrrolidone:water solution containing roflumilast in excess of drug saturation compared to a 12:4:3 (wt/wt/wt) blend of hexylene glycol:N-methyl pyrrolidone:water (1.2 mole fraction of water) solution having roflumilast added in excess of the solubility limit.

Figure 9:
FIG. 9 shows Sample 20-1 roflumilast crystals suspended in equimolar NMP:water solution after storage for six weeks at room temperature. The roflumilast crystals are 0.10 mm-1.55 mm in length and 0.02 mm-0.13 mm in width.

0.0202 grams of roflumilast (Batch A14367P from Interquim S.A.) was mixed with 0.0682 grams of equimolar N-Methyl-2-pyrrolidone:water blend in a liquid scintillation vial. An equimolar blend is 84.5% N-Methyl-2-pyrrolidone (lot SYYN-HJ, TCI) and 15.5% water on a weight/weight percent basis. The 22.85% roflumilast in equimolar N-Methyl-2 pyrrolidone:water was completely dissolved at 25° C. This sample (labeled 13-2) was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 4× objective (FIG. 9, microscope sample 20-1).

Figure 10:
FIG. 10 shows Sample 21-1 roflumilast crystals suspended in HG:NMP:Water (water mole fraction=1.2) solution after storage for six weeks at room temperature. The roflumilast crystals are 0.02 mm-0.04 mm in length and 0.02 mm in width.

A 0.8152 gram sample of 3.6% roflumilast (Batch A14367P from Interquim S.A.), 60.8% hexylene glycol (lot 1AC0818, Spectrum), 20.0% N-Methyl-2-pyrrolidone (lot SYYN-HJ, TCI) and 15.6% distilled water was mixed on a weight/weight percent basis. This sample (labeled 13-4) was a finely dispersed suspension of roflumilast at 25° C. The sample was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 10, microscope sample 21-1).

Example 4

Roflumilast creams were prepared according to the following formulations.

Formulation 1 (Comparative)

| | |
|---|---|
| Roflumilast | 0.5% w/w |
| White Petrolatum | 10.0% w/w |
| Isopropyl Palmitate | 5.0% w/w |
| Crodafos CES | 10.0% w/w |
| Diethylene glycol monoethyl ether (Transcutol P) | 25% w/w |
| Methylparaben | 0.2% w/w |
| Propylparaben | 0.05% w/w |
| Purified Water | q.s. ad 100 (49.25%) |

Formulation 2

| | |
|---|---|
| Roflumilast | 0.5% w/w |
| White Petrolatum | 10.0% w/w |
| Isopropyl Palmitate | 5.0% w/w |
| Crodafos CES | 10.0% w/w |
| Hexylene glycol | 2.0% w/w |
| Diethylene glycol monoethyl ether (Transcutol P) | 25.0% w/w |
| Methylparaben | 0.2% w/w |
| Propylparaben | 0.05% w/w |
| Purified Water | q.s. ad 100 (47.25%) |

Figure 11A:
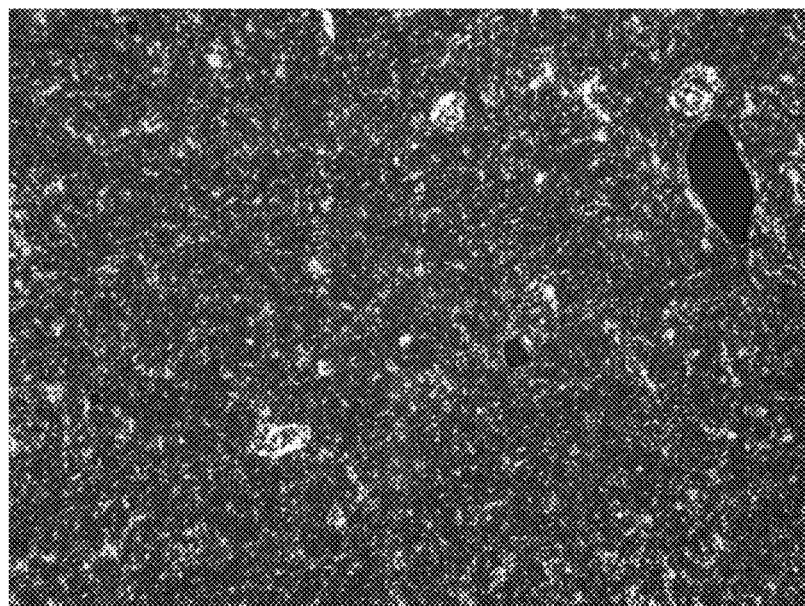
FIGS. 11A and 11B show roflumilast particles precipitated in a cream composition after one freeze thaw cycle.
Figure 11B:
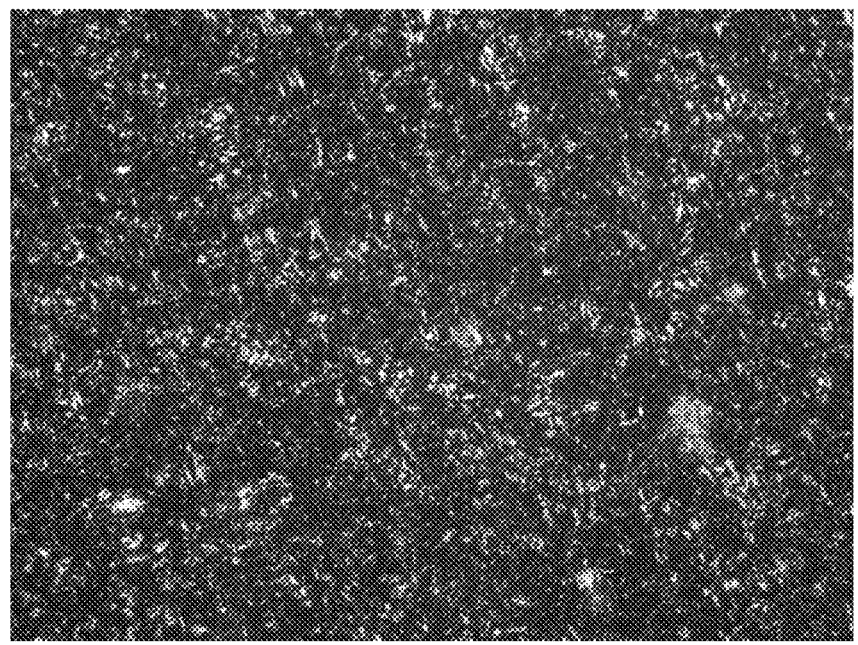

After preparation, 0.4222 grams of formulation 1 was sealed in a 1.0 mL CryoTube™ vial and labeled as 36-1. Likewise, 0.3961 grams of formulation 2 was sealed in a 1.0 mL CryoTube™ vial and labeled as 36-2. The two CryoTube™ vials were secured in an envelope end-to-end and placed in the freezer for 17.5 hours. Quickly upon removal from the freezer, a microscopic slide was prepared of each sample and after "thawing" the sample to room temperature (18° C.) a photomicrograph images was captured to characterize differences in precipitated roflumilast crystal growth. See FIGS. 11A and 11B.

Example 5

A formulation of the invention, hereafter referred to as Formulation 3, was made by combining roflumilast at a concentration of 0.3% w/w with Crodafos CES (the phosphate ester surfactant blend of dicetyl phosphate and ceteth-10 phosphate combined with cetostearyl alcohol) and adding diethylene glycol monoethyl ether, as well as other ingredients to create a complete marketable formulation. This formulation was buffered with NaOH to obtain a pH of 5.5. and water. Formulation 3 is the same as formulation 2 except that formulation 3 contains 0.3% roflumilast and formulation 2 contains 0.5% roflumilast.

A formulation that is not of the invention, hereafter referred to as Comparative Formulation 4, was made by combining roflumilast at a concentration of 0.3% w/w with Crodafos CES (the phosphate ester surfactant blend of dicetyl phosphate and ceteth-10 phosphate combined with cetostearyl alcohol) and water. The formulation was buffered with NaOH to obtain a pH of 5.5. Comparative Formulation 4 does not contain diethylene glycol monoethyl ether or hexylene glycol.

A formulation that is not of the invention, hereafter referred to as Comparative Formulation 5, was made by combining roflumilast at a concentration of 0.2%. This formulation is that of the closest prior art known to the inventors and is disclosed in Example 3 of Bolle et al, U.S. Patent Application No. US 2006/0084684.

A formulation that is not of the invention, hereafter referred to as Comparative Formulation 6, was made by combining roflumilast at a concentration of 0.3%. This formulation contains the phosphate ester potassium cetyl phosphate (Crodafos MCK) as the emulsifier but does not contain dicetyl phosphate or ceteth-10 phosphate which are the phosphate ester emulsifiers contained in the self-emulsifying wax Crodafos CES.

The compositions of these formulations are shown below in Table 1.

| | Formulation 3 | Comparative Formulation 4 | Comparative Formulation 5 | Comparative Formulation 6 |
|---|---|---|---|---|
| Roflumilast | 0.3% w/w | 0.3% w/w | 0.2% w/w | 0.3% w/w |
| Petrolatum | 10.0% w/w | — | — | 10.0% w/w |
| Isopropyl Palmitate | 5.0% w/w | — | — | 5.0% w/w |
| Medium-Chain Triglycerides | — | — | 25.0% w/w | — |
| Dicetyl Phosphate/Ceteth-10 Phosphate | 2-4% w/w* | 2-4% w/w* | — | — |

-continued

|  | Formulation 3 | Comparative Formulation 4 | Comparative Formulation 5 | Comparative Formulation 6 |
|---|---|---|---|---|
| Cetostearyl Alcohol | 6-8% w/w* | 6-8% w/w* | 5.0% w/w | 6.0% w/w |
| Potassium Cetyl Phosphate | — | — | — | 2.0% w/w |
| Glyceryl Stearate/PEG-100 Stearate | — | — | 5.0% w/w | — |
| Diethylene Glycol Monoethyl Ether | 25.0% w/w | — | — | 25.0% w/w |
| Hexylene Glycol | 2.0% w/w | — | — | 2.0% w/w |
| Methylparaben | 0.20% w/w | — | — | 0.20% w/w |
| Propylparaben | 0.050% w/w | — | — | 0.050% w/w |
| 1N NaOH | q.s. ad pH 5.5 | q.s. ad pH 5.5 | — | q.s. ad pH 5.5 |
| Purified Water | q.s. ad 100% | q.s. ad 100% | q.s. ad 100% | q.s. ad 100% |

*The exact ratio of cetostearyl alcohol to dicetyl phosphate to cetheth-10 phosphate in Crodafos CES is consistent between batches of product but is not publicly disclosed by the manufacturer (Croda). The safety data sheet for Crodafos CES states that this emulsifier is composed of 60-80% cetostearyl alcohol, 10-20% dicetyl phosphate and 10-20% cetheth-10 phosphate. To emphasize the similarity in composition between Formulation 5 (phosphate-ester surfactant blend) and Formulation 6 (nonionic surfactant blend), the cetostearyl alcohol portion of Crodafos CES is listed separately from the surfactant portion of Crodafos CES in Table 2.
Glyceryl Stearate/PEG-100 Stearate is the nomenclature used by the US Food and Drug Administration to describe the nonionic emulsifier blend sold using the tradename Arlacel ® 165 and Tego Care ® 165.
Medium-Chain Triglycerides is the nomenclature used by the US Food and Drug Administration to describe the cosmetic ingredient Capryli/Capric Triglyceride which is sold using tradenames including Miglyol ® 812 and Crodamol ® GTCC.

Example 6—Elimination Kinetics after 14-Day Dosing of Formulations of Example 5

Male and female swine (Gottingen Minipig® breed) are ordered to weigh 8 to 12 kg at arrival. On the day prior to administration of one of the topical cream semisolid formulations of Example 5, the hair is clipped from the back of each animal. The pigs are sedated for the shaving procedure. Care is taken to avoid abrading the skin.

Two (2) grams of one of the cream formulations of Example 5 for each kg of pig weight is distributed over the clipped skin area by gentle inunction with a glass stirring rod or stainless-steel spatula. The cream formulation is applied evenly with a thin, uniform film beginning at the scapular region and moving caudally over the test site. The width of the test site area is bilaterally divided by the spine. Six pigs (3 males and 3 females) are dosed with either Formulation 3, Comparative Formulation 4, Comparative Formulation 5 or Comparative Formulation 6 once daily for 14-days. Blood is sampled from the anterior vena cava through the thoracic inlet or other suitable vein on days 17, 18, 19 and 20 days after the last dose administration to determine the elimination half-life of roflumilast from these four cream formulations.

As shown in Table 2, the formulation containing the phosphate ester surfactant Crodafos CES, hexylene glycol and the solvent diethylene glycol monoethyl ether showed significant increase in the plasma half-life and duration of effect of roflumilast after topical application. The closest prior art formulation (Comparative Formulation 5) and Comparative Formulation 6, a cream formulation that replaced Crodafos CES (the phosphate ester surfactant blend of dicetyl phosphate and ceteth-10 phosphate combined with cetostearyl alcohol) with Crodafos MKC (the phosphate ester surfactant potassium cetyl phosphate combined with cetostearyl alcohol) had decreased plasma half-lives compared to Formulation 3 that contained Crodafos CES. Comparative Formulation 4 that did not combine hexylene glycol and diethylene glycol monoethyl ether with the phosphate ester surfactant blend of dicetyl phosphate and ceteth-10 phosphate combined with cetostearyl alcohol (Crodafos CES) did not have an increased half-life and duration of roflumilast effect after topical application in pigs.

TABLE 2

|  | Formulation 3 | Comparative Formulation 4 | Comparative Formulation 5 | Comparative Formulation 6 |
|---|---|---|---|---|
| $t_{1/2}$ | 4.5 days | 2.5 days | 2.8 days | 2.4 days |

Example 7—Elimination Kinetics after 84-Day Dosing of Formulation 3 in Psoriatic Patients A roflumilast cream was prepared according to the following formulation.
Formulation 7

| Roflumilast | 0.15% w/w |
|---|---|
| White Petrolatum | 10.0% w/w |
| Isopropyl Palmitate | 5.0% w/w |
| Crodafos CES | 10.0% w/w |
| Hexylene glycol | 2.0% w/w |
| Diethylene glycol monoethyl ether (Transcutol P) | 25.0% w/w |
| Methylparaben | 0.2% w/w |
| Propylparaben | 0.05% w/w |
| Purified Water | q.s. ad 100 (47.6%) |

A parallel group, double blind, vehicle-controlled study was performed in which ARQ-151 cream 0.3% (Formulation 3 in Example 5) or ARQ-151 cream 0.15% (Formulation 7) or vehicle cream is applied QD for 84 days to subjects with chronic plaque psoriasis involving between 2 and 20% body surface area (BSA).

A total of approximately 300 subjects were enrolled at approximately 30 study sites in the United States and Canada. Subjects were adult (≥18 y/o) males or females with chronic plaque psoriasis. Subjects had an Investigator's Global Assessment of disease severity (IGA) of at least Mild ('2') at Baseline. Subjects with an IGA of 'Mild' (2) were limited to 20% of total enrollment. Subjects with an IGA of 'Severe' (4) were limited to 15% of total enrollment. Subjects had at least 2% and no more than 20% Body Surface Area (BSA) of chronic plaque psoriasis. All psoriasis lesions on a subject were treated including the face, trunk, genitals/skin folds, or limbs (excluding the scalp). The palms and soles were treated but were not counted towards any measurements of efficacy (IGA, BSA, mPASI). For subjects with intertriginous area involvement, and with severity of the intertriginous area lesions at least 'mild' (IGA≥2) at Baseline, 'I-IGA' score was recorded at weeks 4, 6, 8 and 12. The same IGA used for the primary endpoint (whole body) was also used for 'intertriginous area lesion IGA score' (I-IGA), but only intertriginous areas were evaluated for I-IGA, not the rest of the body.

Blood samples were taken from all subjects at all sites as pre-dose on Day 1 (baseline) and Weeks 4 (Day 29) and 12 (Day 85). The analysis of the PK data collected was performed with a CFR 21 Part 11 compliant software package (Phoenix WinNonlin version 8.1) which is in full compliance with ICH-GCP. Samples from all subjects within the PK population were evaluated. Any subject or data excluded from the PK analysis were identified, along with the reason for exclusion in this PK report. BSA was averaged based on Baseline, Week 2, Week 4, Week 6 and Week 8 measured BSA values, the screening values, Week 12 and Week 16 values, and any other unscheduled visit values were excluded. Four subjects participated in an optional phase at the completion of the study to assess the elimination of roflumilast and the N-oxide at the end of treatment, however only three had quantifiable concentrations of roflumilast and the N-oxide. From the three subjects, the terminal rate constant (lambda z, λz) was determined by the slope of the regression line of the natural log transformed concentrations vs. time data. The terminal half-life (t1/2) was calculated as: $\ln(2)/\lambda z$.

Concentration values that are reported BLQ (<0.100 for roflumilast and N-oxide) were reported as below limit of quantification (BLQ) in the concentration data listings and considered non-numerical. Nonnumerical values were ignored in the concentration by nominal time summary statistics. Summary statistics (i.e. N, arithmetic mean, SD, CV %, minimum, median, maximum, geometric mean, geometric SD, 95% confidence intervals for both the arithmetic mean and geometric mean) were calculated for plasma concentrations for each analyte, nominal day and dose strength. All concentration and descriptive statistic values were reported to three significant figures.

Following multiple topical administrations of ARQ-151 to areas of plaque psoriasis covering between 2 to 20% BSA, evidence of systemic plasma exposure to roflumilast and the N-oxide was observed (Table 3). Mean BSA treated was approximately 5% for both treatment groups (Table 3). Mean roflumilast pre-dose concentrations were 1.82 and 1.50 ng/mL following topical administration of ARQ-151 0.3% on Day 29 and Day 85, respectively (Table 3). Normalizing the BSA treated, the mean concentration values were 0.424 and 0.344 ng/mL, respectively. Mean roflumilast pre-dose concentrations were 1.12 and 0.878 ng/mL following topical administration of ARQ-151 0.15% on Day 29 and Day 85, respectively. Normalizing the BSA treated, the mean concentration values were 0.293 and 0.250 ng/mL, respectively.

Mean N-oxide pre-dose concentrations were 11.2 and 9.18 ng/mL following topical administration of ARQ-151 0.3% on Day 29 and Day 85, respectively. Normalizing the BSA treated, the mean concentration values were 2.66 and 2.10 ng/mL, respectively. Mean N-oxide pre-dose concentrations were 6.53 and 4.63 ng/mL following topical administration of ARQ-151 0.15% on Day 29 and Day 85, respectively. Normalizing the BSA treated, the mean concentration values were 1.68 and 1.28 ng/mL, respectively. Overall, mean roflumilast and the N-oxide pre-dose plasma concentration values were within 2-fold of each other on Day 29 and Day 85.

The arithmetic mean (AM) Day 15 pre-dose concentrations following topical administration of ARQ-151 0.15% in patients with atopic dermatitis with a mean BSA treated area of 6.5% (n=6) was 1.99 ng/mL (Study ARQ-151-102), dose normalized of 0.306 ng/mL. The geometric mean (GM) value was 0.874 ng/mL with a normalized value of 0.134 ng/mL. Comparison to the Day 29 dose normalized pre-dose concentration values in this study following 0.15% administration in subjects with plaque psoriasis treating 5% BSA (AM value of 0.293 ng/mL and GM value of 0.187 ng/mL) were within 10% of each other suggesting minimal differences in systemic exposure between the 2 disease states. Because of the flat nature of the plasma concentrations at steady state, AUC values can be extrapolated by multiplying the pre-dose concentration by 24. From the ARQ-151-102 study, the AM AUClast value was 53.9 with a GM value of 21.9 h*ng/mL. Using the AM and GM pre-dose values, an extrapolated AUC value for the ARQ-151-102 study, would be 47.8 or 21.0 h*ng/mL—which is in good alignment with the measured values. From this study, using the Day 29 pre-dose concentrations, the extrapolated AM and GM AUC values would be 26.9 and 18.6 h*ng/mL Roflumilast plasma pre-dose concentration values increase about 1.6- and 1.7-fold on Day 29 and Day 85, respectively between the 2-fold increase in dose strength. Similarly, the roflumilast N-oxide (N-oxide) plasma pre-dose concentration values increase about 1.7- and 2.0-fold on Day 29 and Day 85, respectively between the 2-fold increase in dose strength.

In general, the mean N-oxide pre-dose plasma concentrations were 5.3- to 6.2-fold higher than the parent pre-dose plasma concentrations, which is consistent with previous studies.

Three subjects participated in an optional phase of the completion of the study to assess the elimination of roflumilast and the N-oxide at the end of treatment. Half-life values were around 3.6 days for both roflumilast and the N-oxide (see Table 4).

TABLE 3

Summary Roflumilast and N-oxide Plasma Pre-dose Concentrations Following Topical Administration of ARQ-151

| | | | BSA | | Roflumilast | | | | Roflumilast N-Oxide | | | |
| | | | Day 29 | Day 85 | Day 29 | | Day 85 | | Day 29 | | Day 85 | |
| | Treatment | | | | Conc (ng/mL) | Conc/BSA (ng/mL) | Conc (ng/mL) | Conc/BSA (ng/mL) | Conc (ng/mL) | Conc/BSA (ng/mL) | Conc (ng/mL) | Conc/BSA (ng/mL) |
|---|---|---|---|---|---|---|---|---|---|---|---|---|
| 0.3% | N | | 97 | 92 | 9 | 94 | 82 | 82 | 96 | 9 | 88 | 88 |
| | Mean | | 4.92 | 4.91 | 1.82 | 0.424 | 1.50 | 0.344 | 11.2 | 2.66 | 9.18 | 2.10 |
| | SD | | 3.77 | 3.85 | 2.47 | 0.482 | 1.99 | 0.327 | 17.4 | 3.10 | 12.1 | 1.94 |
| | CV % | | 76.7 | 78.4 | 136 | 114 | 133 | 94.9 | 155 | 117 | 131 | 92.2 |
| | Min | | 0.640 | 0.640 | 0.106 | 0.0212 | 0.10 | 0.0184 | 0.47 | 0.128 | 0.11 | 0.0159 |

TABLE 3-continued

Summary Roflumilast and N-oxide Plasma Pre-dose Concentrations Following Topical Administration of ARQ-151

| | | | | Roflumilast | | | | Roflumilast N-Oxide | | | |
| --- | --- | --- | --- | --- | --- | --- | --- | --- | --- | --- | --- |
| | | | | Day 29 | | Day 85 | | Day 29 | | Day 85 | |
| | | BSA | | Conc | Conc/BSA | Conc | Conc/BSA | Conc | Conc/BSA | Conc | Conc/BSA |
| | Treatment | Day 29 | Day 85 | (ng/mL) | (ng/mL) | (ng/mL) | (ng/mL) | (ng/mL) | (ng/mL) | (ng/mL) | (ng/mL) |
| | Median | 3.90 | 3.80 | 1.09 | 0.261 | 0.94 | 0.221 | 6.97 | 1.58 | 6.09 | 1.41 |
| | Max | 20.0 | 20.0 | 18.9 | 2.78 | 16.0 | 2.18 | 152 | 22.4 | 86.3 | 8.21 |
| | Geometric Mean | 3.94 | 3.89 | 1.02 | 0.258 | 0.95 | 0.235 | 6.43 | 1.65 | 5.13 | 1.30 |
| | Geometric SD | 1.92 | 1.95 | 2.99 | 2.77 | 2.56 | 2.49 | 2.88 | 2.70 | 3.17 | 3.08 |
| | CI 95% Lower Mean | 4.16 | 4.11 | 1.31 | 0.326 | 1.06 | 0.272 | 7.71 | 2.03 | 6.63 | 1.69 |
| | CI 95% Upper Mean | 5.68 | 5.70 | 2.32 | 0.523 | 1.94 | 0.416 | 14.8 | 3.28 | 11.7 | 2.52 |
| | CI 95% Lower GEO Mean | 3.46 | 3.39 | 0.816 | 0.209 | 0.77 | 0.193 | 5.19 | 1.35 | 4.02 | 1.02 |
| | CI 95% Upper GEO Mean | 4.50 | 4.47 | 1.28 | 0.318 | 1.17 | 0.288 | 7.97 | 2.02 | 6.55 | 1.65 |
| 0.15% | N | 102 | 96 | 89 | 89 | 84 | 84 | 99 | 99 | 92 | 92 |
| | Mean | 4.89 | 4.76 | 1.12 | 0.293 | 0.878 | 0.250 | 6.53 | 1.68 | 4.63 | 1.28 |
| | SD | 3.32 | 3.38 | 1.01 | 0.326 | 1.08 | 0.389 | 7.00 | 2.08 | 4.37 | 1.46 |
| | CV % | 67.8 | 71.1 | 90.9 | 111 | 124 | 156 | 107 | 124 | 94.2 | 114 |
| | Min | 0.800 | 0.800 | 0.104 | 0.0137 | 0.110 | 0.0225 | 0.129 | 0.0269 | 0.246 | 0.0330 |
| | Median | 4.00 | 3.60 | 0.821 | 0.211 | 0.620 | 0.124 | 4.05 | 0.935 | 3.40 | 0.764 |
| | Max | 20.0 | 20.0 | 4.65 | 2.08 | 8.76 | 3.20 | 37.5 | 13.3 | 22.8 | 7.74 |
| | Geometric Mean | 4.00 | 3.86 | 0.776 | 0.187 | 0.577 | 0.146 | 3.99 | 1.00 | 3.05 | 0.785 |
| | Geometric SD | 1.90 | 1.91 | 2.41 | 2.65 | 2.48 | 2.67 | 2.93 | 2.89 | 2.68 | 2.76 |
| | CI 95% Lower Mean | 4.24 | 4.07 | 0.903 | 0.225 | 0.643 | 0.165 | 5.13 | 1.27 | 3.73 | 0.973 |
| | CI 95% Upper Mean | 5.54 | 5.44 | 1.33 | 0.362 | 1.11 | 0.334 | 7.92 | 2.10 | 5.54 | 1.58 |
| | CI 95% Lower GEO Mean | 3.53 | 3.39 | 0.645 | 0.152 | 0.474 | 0.118 | 3.22 | 0.810 | 2.49 | 0.636 |
| | CI 95% Upper GEO Mean | 4.54 | 4.40 | 0.934 | 0.229 | 0.703 | 0.180 | 4.94 | 1.24 | 3.75 | 0.969 |

TABLE 4

Plasma Concentration Data from Subjects that Participated in Optional Elimination Phase Assessment Following Topical Administration of ARQ-151

| | | | | Plasma Concentration (ng/mL) by Time (h) | | | | | $t_{1/2}$ |
| --- | --- | --- | --- | --- | --- | --- | --- | --- | --- |
| Analyte | Treat | Subject | BSA | 0 | 72 | 120 | 168 | 216 | (day) |
| Rof | 0.3% QD | 19004 | 8.8 | 0.483 | | 0.127 | 0.460 | | N/C |
| | | 19011 | 4.2 | 0.689 | 0.567 | 0.230 | 0.195 | 0.123 | 3.4 |
| Rof | 0.15% QD | 19009 | 4.0 | 0.135 | 0.117 | BLQ* | | BLQ | 3.7* |
| N-Oxide | 0.3% QD | 19004 | 8.8 | 6.81 | | 2.19 | 2.35 | | 4.2 |
| | | 19011 | 4.2 | 3.91 | 3.49 | 1.94 | 1.03 | 0.796 | 3.5 |
| N-Oxide | 0.15% QD | 19009 | 4.0 | 0.685 | 1.02 | 0.809 | | 0.272 | 3.0 |

*To assess half = life, the first BLQ value was set equal to 0.05 ng/mL

As noted above the plasma half-life of roflumilast after intravenous administration is about 15 hours; after oral administration the plasma half-life is about 17-30 hours. The plasma half-life of roflumilast after topical administration of a formulation comprising hexylene glycol, diethylene glycol monoethyl ether (Transcutol P) and a self-emulsifying wax blend of dicetyl phosphate and ceteth-10 phosphate is 3.4-3.7 days (about 81-89 hours). The increased half-life and duration of effect removes the concern that adherence imperfection will decrease therapeutic success and increases the adherence imperfection forgiveness of topically applied roflumilast.

The invention claimed is:

1. A method of treating inflammatory dermatoses comprising topically administering a pharmaceutical composition comprising:
   (i) roflumilast in an amount of 0.05-1.0% w/w;
   (ii) diethylene glycol monoethyl ether; and
   (iii) an emulsifier blend comprising cetostearyl alcohol, dicetyl phosphate and ceteth-10 phosphate; and
   (iv) water,
   wherein the composition is administered once daily.

2. The method according to claim 1, wherein said composition comprises 1.0-25% w/w of said emulsifier blend.

3. The method according to claim 2, wherein said composition is a cream, and wherein said composition comprises 2.5-20% w/w of said emulsifier blend.

4. The method according to claim 3, wherein said composition comprises 5-15% w/w of said emulsifier blend.

5. The method according to claim 4, wherein said composition comprises 10% w/w of said emulsifier blend.

6. The method according to claim 2, wherein said composition is a foam, and wherein said composition comprises 1.0-10% w/w of said emulsifier blend.

7. The method according to claim 6, wherein said composition comprises 2% w/w of said emulsifier blend.

8. The method according to claim 1, wherein said composition comprises 10-30% w/w diethylene glycol monoethyl ether.

9. The method according to claim 8, wherein said composition comprises 25% w/w diethylene glycol monoethyl ether.

10. The method according to claim 1, wherein said inflammatory dermatoses is psoriasis.

11. The method according to claim 10, wherein said composition is applied to psoriasis lesions in intertriginous areas.

12. The method according to claim 11, wherein said composition comprises 1.0-25% w/w of said emulsifier blend and 10-30% w/w diethylene glycol monoethyl ether.

13. The method according to claim 12, wherein said composition comprises 10% w/w of said emulsifier blend.

14. The method according to claim 10, wherein said composition is applied to psoriasis lesions on the scalp.

15. The method according to claim 14, wherein said composition comprises 1.0-25% w/w of said emulsifier blend and 10-30% w/w diethylene glycol monoethyl ether.

16. The method according to claim 15, wherein said composition comprises 2% w/w of said emulsifier blend.

17. The method according to claim 1, wherein said inflammatory dermatoses is atopic dermatitis.

18. The method according to claim 17, wherein said composition comprises 1.0-25% w/w of said emulsifier blend and 10-30% w/w diethylene glycol monoethyl ether.

19. The method according to claim 18, wherein said composition comprises 10% w/w of said emulsifier blend.

20. The method according to claim 1, wherein said inflammatory dermatoses is seborrheic dermatitis.

21. The method according to claim 20, wherein said composition comprises 1.0-25% w/w of said emulsifier blend and 10-30% w/w diethylene glycol monoethyl ether.

22. The method according to claim 21, wherein said composition comprises 2% w/w of said emulsifier blend.

* * * * *